United States Patent [19]
Koopal et al.

[11] Patent Number: 5,422,246
[45] Date of Patent: Jun. 6, 1995

[54] ELECTRODE HAVING A POLYMER COATING WITH A REDOX ENZYME BOUND THERETO, THE POLYMER COATING BEING FORMED ON THE WALLS OF PORES EXTENDING THROUGH A POROUS MEMBRANE

[75] Inventors: Cornelis G. J. Koopal, Zeist; Richardus B. M. Schasfoort, Amersfoort; Roeland J. M. Nolte, Nijmegen, all of Netherlands

[73] Assignee: Nederlandse Organisatie Voor Toegepast-Natuurwetenschappelijk Onderzoek Tno, Delft, Netherlands

[21] Appl. No.: 75,509
[22] PCT Filed: Dec. 13, 1991
[86] PCT No.: PCT/NL91/00263
§ 371 Date: Jun. 14, 1993
§ 102(e) Date: Jun. 14, 1993
[87] PCT Pub. No.: WO92/10584
PCT Pub. Date: Jun. 25, 1992

[30] Foreign Application Priority Data

Dec. 14, 1990 [NL] Netherlands ............. 9002764

[51] Int. Cl.⁶ ................. C12Q 1/54; C12M 1/40
[52] U.S. Cl. ....................... 435/14; 435/25; 435/288; 435/291; 435/817; 205/164; 204/403; 204/153.12
[58] Field of Search ........... 435/14, 25, 28, 288, 435/291, 817; 204/59 R, 72, 153.12, 403; 205/67, 159, 160, 164, 317; 436/95, 151; 548/564

[56] References Cited

U.S. PATENT DOCUMENTS

| | | | |
|---|---|---|---|
| 4,582,575 | 4/1986 | Warren et al. | 204/12 |
| 4,589,575 | 4/1986 | Warren | 205/55 |
| 4,891,104 | 1/1990 | Liston | 204/1 |
| 4,976,860 | 12/1990 | Takahashi | 210/500.28 |
| 5,066,706 | 11/1991 | Destryker | 524/459 |
| 5,200,051 | 4/1993 | Cozzette | 204/403 |
| 5,202,261 | 4/1993 | Musho | 435/288 |
| 5,215,682 | 6/1993 | Destryker | 252/519 |
| 5,250,439 | 10/1993 | Musho | 435/25 |

FOREIGN PATENT DOCUMENTS 59-164953 9/1984 Japan.
63-218850 9/1988 Japan.

OTHER PUBLICATIONS

Umana, M. Protein Modified Electrodes . . . ACS 1986 pp. 2979–2983.
Fortier G., Optimization of a Polypyrrole Glucose Oxidase Biosensor, Biosens. & Bioelectr. 5(1990) pp. 473–490.
"Protein-Modified Electrodes. The Glucose Oxidase-/Polypyrrole System", *American Chemical Society*, 1986, by M. Umana et al., pp. 2979–2983.

(List continued on next page.)

Primary Examiner—William H. Beisner
Assistant Examiner—Ralph Gitomer
Attorney, Agent, or Firm—Young & Thompson

[57] ABSTRACT

An electrode is composed of a membrane, provided with open pores running through said membrane, the walls of the pores having an electrically conducting polymer coating, containing a redox enzyme bound thereto. In these type of electrodes a direct electron transfer is possible between the redox enzyme, e.g. glucose oxidase, and the electrically conducting polymer, e.g. polypyrrole. Such an electrode, which can be produced in a simple manner, has extensive application possibilities such as, for example, in a biosensor or in a production installation for the preparation of specific chemicals. As starting materials for the electrodes of the invention, use can be made of marketed porous membrane materials as well as of latex particles. The walls of the pores of porous membrane and the interstices of the latex particles respectively are provided with a thin layer of the electrically conducting polymer which in turn is provided with a redox enzyme suitable for the pursued aim.

16 Claims, 17 Drawing Sheets

OTHER PUBLICATIONS

"Electropolymerized 1,2-Diaminobenzene as a Means to Prevent Interferences and Fouling and To Stabilize Immobilized Enzyme in Electrochemical Biosensors", *American Chemical Society*, by S. Sasso et al., pp. 1111–1117, 1990 Jun.

"Optimization of a Polypyrrole Glucose Oxidase Biosensor", *Biosensores & Bioelectronics*, vol. 5, 1990, By G. Fortier et al. pp. 473–490.

"Enzyme Entrapped Polypyrrole Modified Electrode for Flow–Injection Determination of Glucose", *Biosensors & Bioelectronics*, vol. 5, 1990, By M. Trojanowicz et al., pp. 149–156.

"Characterisation of the Structure of Inorganic Chloride Salts with Chlorine Solid State N.M.R.", *Journal of Chemical Society*, By T. Weeding et al., pp. 945 and 946, 1989.

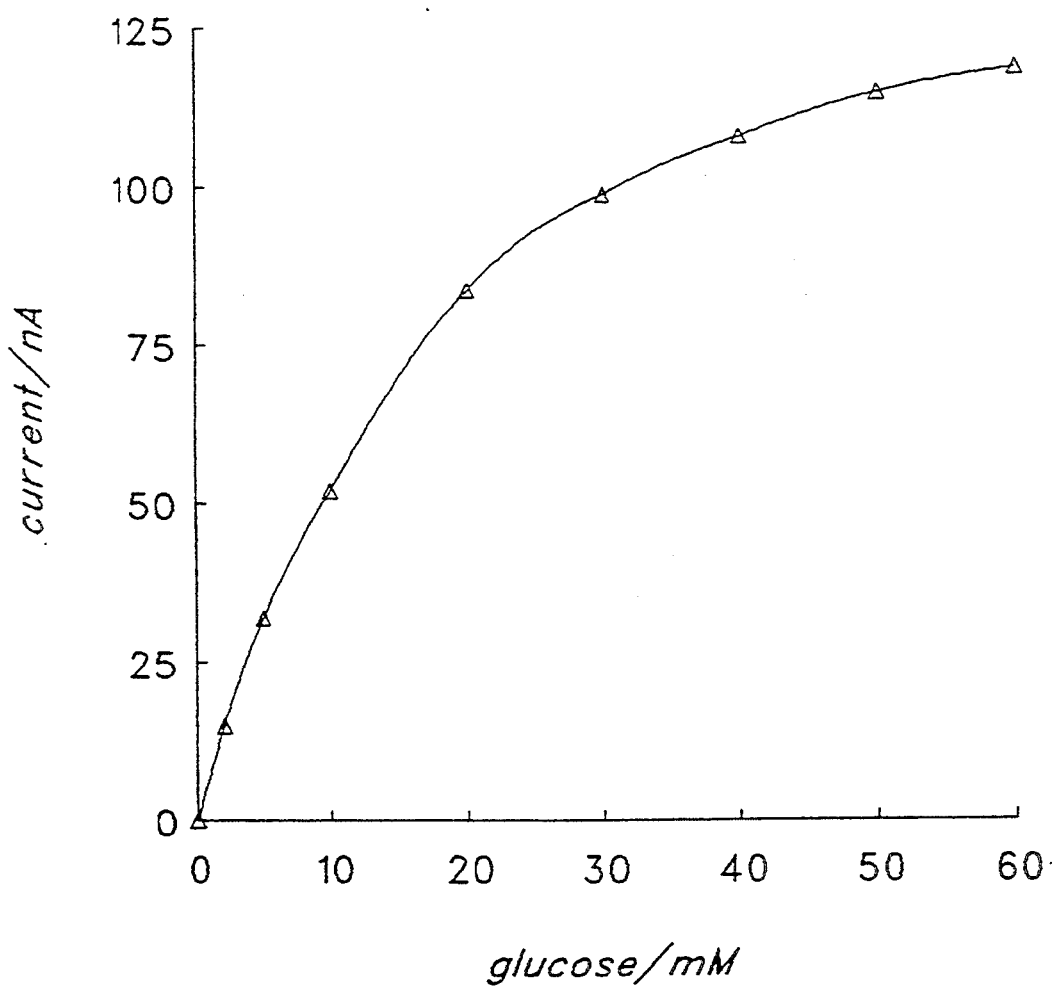

ELECTRODE HAVING A POLYMER COATING WITH A REDOX ENZYME BOUND THERETO, THE POLYMER COATING BEING FORMED ON THE WALLS OF PORES EXTENDING THROUGH A POROUS MEMBRANE

The invention relates to an electrode which is provided with a polymer coating having a redox enzyme bound thereto and which electrode, depending on the chosen aim, can be used either in a biosensor for the specific detection of certain substances recognisable to the particular enzyme or in the production of chemicals which can be prepared by the particular enzyme. The invention also relates to biosensors and production installations for chemicals, which contain such as electrode.

A biosensor of the type described above is disclosed in Anal. Chem. 1990, 62. pp. 1111-1117. More particularly, this literature reference relates to a platinum-plated carbon electrode, which is provided with the redox enzyme glucose oxidase and a layer of polymerised 1,2-diaminobenzane applied by means of electropolymerisation. Using a glucose sensor of this type, based on flavin adenine dinucleotide (FAD)-bound glucose oxidase (GOd, the glucose to be detected is determined indirectly with the aid of the liberated hydrogen peroxide, as is illustrated by the reaction equations given below:

$$GOd\text{-}FAD + glucose \rightarrow GOd\text{-}FADH_2 + gluconolactone$$

$$GOd\text{-}FADH_2 + O_2 \rightarrow GOd\text{-}FAD + H_2O_2$$

However, the detection of this hydrogen peroxide, which is detected at the anode, has the disadvantage that said detection must be carried out under high voltages applied to the sensor, which can give rise to interference by other substances. Moreover, the hydrogen peroxide has a degrading action on the glucose oxidase used as redox enzyme (see p. 1112, left hand column, paragraph three). In addition, it is pointed out that an immobilisation of the glucose oxidase preferably takes place using a carbodiimide as agent providing covalent bonds and/or glutaraldehyde as crosslinking agent, which makes the production of such a biosensor fairly laborious.

In Acc. Chem. Res. 23 (1990), pp. 128-134 the use of small diffusing mediators such as, for example, ferrocene and ferrocene 7 derivatives, as synthetic electron acceptor for redox enzymes is reported. In the case of glucose oxidase, the glucose to be detected is determined indirectly via the (reduced) mediator; see the reaction equations below:

$$GOd\text{-}FAD + glucose \rightarrow GOd\text{-}FADH_2 + gluconolactone$$

$$GOd\text{-}FADH_2 + 2\ mediator^{ox} \rightarrow GOd\text{-}FAD + 2\ mediator^{red} + 2H^+$$

The reduced mediator obtained is then oxidised electrochemically. However, it has been found that the use of a mediator is associated with disadvantages such as the leakage of the mediator from the system. Moreover, suitable mediators often have toxic characteristics. This severely restricts the field of application of sensors based thereon.

Sensors and Actuators B1 (1990), pp. 537-541 discloses the use of a polypyrrole file applied to an electrode surface, which film is bonded convalently, via a carbodiimide activation, with redox enzymes such as glucose oxidase and the like. Biosensors having a relatively short response time are obtained in this way. However, in the production of such biosensors a carbodiimide is required as reagent, the use of which is found to be undesirable.

Biotechnol. Bioeng. (1988), 31, 6, 3/2, 553-558 discloses an electrocatalysis reactor in which glucose oxidase is used as redox enzyme. This glucose oxidase is applied to the surface of carbon felt by means of carrying out an interface oxidation of the carbon in order to form carboxylic acid groups and an activation of these groups by means of a carbodiimide, followed by immobilisation of the glucose oxidase. A solution of glucose (as starting material for gluconic acid) and benzoquinone (as electron transfer mediator) was passed through the reactor described in this literature reference. The reactor produces gluconic acid from glucose at a rate of about 100 g/hour.liter of reactor. Apart from the specific method of immobilisation of the redox enzyme, the use of the mediator is also found to be not very suitable.

U.S. Pat. No. 4,582,575 relates to electrically conductive composite comprising a dielectric porous substance e.g. fiberglass fabric, and the electrically conducting polymer polypyrrole deposited in the pores and interstices of such substance. Such type of composites which pores and interstices have been impregnated i.e. practically filled with polypyrrole do have—considering the high brittleness of polypyrrole per se—both a good electrical conductivity and good mechanical properties i.e. are essentially non-brittle and readily handleable.

From Analytical Chemistry, Vol. 58, 1966, pages 2979-2983 it is known to immobilize the enzyme glucose oxidase in an electrically conducting polypyrrole matrix by electropolymerizing pyrrole in aqueous media containing glucose oxidase. As appears from page 2982, second paragraph of this reference a simple absorption of glucose oxidase by exposing a preformed polypyrrole film to a glucose oxidase solution is not considered possible as such as treated polypyrrole film present in an oxygen-saturated solution containing glucose, KI, Mo(VI) and buffer does not yield current or iodine formation.

The aim of the invention is to develop an electrode of the type formulated in the preamble, which electrode can be produced in a simple manner and has extensive application possibilities, such as, for example, in a biosensor or in a production installation for the preparation of specific chemicals. A production installation of this type has not yet been described in the literature.

It has been found that the abovementioned aim can be achieved with the aid of an electrode which is composed of a membrane, provided with open pores running through said membrane, the walls of the pores having an electrically conducting polymer coating, which polymer coating present on the wall of the open pores contains a redox enzyme bound thereto. Preferably one side of the membrane is provided with a conducting layer consisting of for instance a metal or carbon, which layer is in contact with the polymer coating.

In general the direct electron transfer between the redox enzyme e.g. glucose oxidase and the conducting polymer occuring in the electrodes according to the invention is illustrated in FIG. 1.

More particularly, within the framework of the invention it can be stated that the Applicant has made use of, on the one hand, the mesoscopic space of the pore and/or interstices containing membranes and, on the other hand, of the morphology of the electrically conducting polymer, by which means it has proved possible to establish an electron transfer, proceeding via the polymer, between the redox enzyme, such as, for example, glucose oxidase, and the electrode and also to incorporate the redox enzyme in the pores while maintaining the activity of said enzyme. It is pointed out that a significant advantage of the subject of the invention is that in this case no auxiliaries known from the prior art, such as carbodiimides, glutaraldehyde and the like, are needed for immobilisation of the redox enzymes.

With regard to the electrode according to the invention it is also pointed out that the redox enzymes present in the pores of the membrane, on the one hand, have a better opportunity for retaining their tertiary structure and, on the other hand, in the pores of the membrane are better screened against external influences, such as shear forces exerted thereon and the influences arising when handling the sensor.

With regard to the electrode according to the invention, the membranes used can be many commercially available inert membrane, such as the commercial products Nuclepore ® membranes, Cyclopore ® membranes, Anopore ® membranes and Millipore ® membranes. More particularly, Nuclepore ® membranes are, for example, polycarbonate or polyester membranes, which membranes are provided with uniform cylindrical pores which pass through the membrane. Like the organic Nuclepore ® membranes, the organic Cyclopore ® membranes and the inorganic Anapore ® membranes also possess pores passing through the membrane. With regard to the thickness of the membrane, it can be stated that this is not critical per se and is usually in the range of 1-20 μm and advantageously about 10 μm. The diameter of the pores present in the membrane can vary within wide limits and is usually in the range of 100-10,000 nm (0.1-10 μ), advantageously in the range of 100-1000 nm. The pores density (number of pores/cm$^2$) is partly dependent on the pore diameter, but is usually in the range of $1 \times 10^5 - 3 \times 10^8$.

Another type of membrane can be manufactured on the basis of latex particles to create porous layers on which polypyrrole can be electrochemically synthesized. Within the interspherical pores of the polypyrrole modified latex layers a redox enzyme like glucose oxidase can be adsorbed irreversibly while its catalytic activity is retained. The latex particles—applicable according to the invention—have a diameter in the range of 50-1000 nm, preferably 50-300 nm. Examples of suitable latex materials are a.o. (monodispers) polystyrene latex, polymethyl methacrylate latex, a silica latex or a latex of a conducting polymer like polypyrrole and polyacetylene. Specific latex examples are Unisphere ® latex particles having a diameter of 50 nm (type 10) or 100 nm (type 11) (Brunschwig Chemie B.V., the Netherlands) and "Polybead" ® polystyrene microspheres having a diameter of 50, 100 and 200 nm respectively (Polysciences Corp. Niles/Ill., USA).

In principle, the electrically conducting polymers used can be the polymers known from the prior art, such as the polymers which are based on pyrrole, substituted pyrrole derivatives, thiophene, substituted thiophene derivatives, aniline and substituted aniline derivatives. Preferably, pyrrole is used as the monomer for the production of an electrically conducting polypyrrole coating. The thickness of the layer applied in the pores partly depends on the diameter of the pores in the membrane, as said pores must still be open following the application of the polymer coating. Usually, polypyrrole coatings having a thickness of 50-200 nm are used, but coatings having a thickness deviating therefrom can also be used.

Diverse types of redox enzymes, for instance oxidases and dehydrogenases, may be mentioned as redox enzymes to be applied in the coated pores of the membrane. Examples of such enzymes are glucose oxidase, lactose oxidase, galactose oxidase, enoate reductase, hydrogenase and choline dehydrogenase. As is known, such enzymes convert to one of an oxidized and reduced form upon reacting with a selected substrate, whereafter the operation of the electrode regenerates the other of the oxidized and reduced forms. Thus, in this invention, the direct electron transfer between the redox enzyme and the conducting polymer effects regeneration, as shown in FIG. 1. Glusose oxidase is advantageously used. This redox enzyme is usually present in an amount of 0.02-0.2 U/cm$^2$ of membrane surface. (1 U (unit) oxidises 1 μmol of β-D-glucose to D-gluconic acid and $H_2O_2$ per minute at pH=5.1 and a temperature of 35° C.). With the aid of redox enzymes of this type, the relevant substances can be either specifically detected (biosensor) or specifically converted to give the relevant reaction products (bio-electrochemical production installation). An example which may be mentioned is β-D-glucose oxidase (E.C. 1.1.3.4 fro Aspergillus niger), with which, on the one hand, glucose can be detected in a specific manner and, on the other hand, β-D-glucose can be converted to D-gluconic acid in a specific manner.

The electrode according to the invention may be provided on at least one side with a conducting layer consisting of for instance a metal or carbon, which layer can connect the electrode to the measuring instrument coupled thereto. Examples of suitable metals for this purpose are, inter alia, platinum, gold and palladium, platinum being preferred. The application of the metal layer can be carried out in a known manner, such as, for example, by means of sputtering, vapour deposition and the like. The thickness of such a metal layer is usually 100-500 nm.

Within the framework of the invention, the electrodes can be produced as follows. The membranes used can be, for example, Nuclepore membranes containing pores having, for example, a diameter of 100-10,000 nm, advantageously 200-8000 nm and preferably 800-1000 nm. The electrically conducting polymer coating can be applied to the pores of the membrane with the aid of an oxidising chemical polymerisation. For this purpose, for example, a pyrrole solution in water (for example 0.3-0.8M pyrrole) and an iron(III) chloride solution in water (1.5-2.5M) are allowed to come into contact with one another, one reagent being placed on one side of the membrane and the other reagent on the other side of the membrane. The pyrrole monomers and the oxidising iron(III) chloride solution meet one another in the pores of the membrane, which results in a polymerisation of the pyrrole. The polymerisation time is not critical and can be, for example, 2-10 min. In this context it is pointed out that the porosity is the main parameter. The polymerisation reaction can be stopped, for example, by rinsing with water or a phosphate buffer solution (PBS: pH=6.5). A polymerisation time appreciably longer than 10 min. leads to nonporous membranes, which are not usable within the framework of the invention. A scanning electron micrograph of a track-etch Cyclopore membrane which pores are coated with the conducting polymer polypyrrole is shown in FIG. 2a.

After applying the electrically conducting polymer coating to the walls of the pores of the membrane and, when necessary, removing any polymer coating on the side(s) of the membrane by, for example, wiping off, a metal layer of platinum or a similar metal may be applied to one side of the membrane by means of, for example, sputtering using an Edwards Sputtercoater S150B.

Finally, the membrane is provided in the pores, the walls of which are coated with an electrically conducting polymer, with a redox enzyme such as glucose oxidase by treating the membrane with a redox enzyme-containing solution, with stirring, at a temperature of, for example, 2°–10° C., advantageously 4° C., for at least 0.1 hour, preferably at least 0.5 hour. The concentration of glucose oxidase in the solution can vary within wide limits and is about 5 mg/ml. Following this treatment, the prepared membranes can be dried overnight in a desiccator over $CaCl_2$.

According to another embodiment of the invention latex membranes may be manufactured by casting latex particles on a freshly sputtered metal (e.g. platinum) surface from an aqueous solution, containing the suspended latex particles and—if desired—agarose. Agarose may be added for better attachment of the latex spheres to each other and to the electrode. Subsequently the latex droplet is dried at low temperature to get a uniform layer without cracks in the surface. After drying, the latex modified electrodes are heat-treated resulting in a membrane consisting of a very strong layer of uniform latex particles.

The amount of agarose present in the latex suspension may be varied to minimize the amount of agarose necessary to yield good latex layers. For instance latex layers were cast from solutions containing 0.125, 0.100, 0.075, and 0.050 wt % agarose respectively. The agarose content of 0.125% led to latex layers which were less accessable for polypyrrole coating. Biosensors constructed from latex layers containing this amount of agarose displayed lower activity and very long response times (see below). Lower amounts than 0.125 wt % of agarose resulted in strong latex layers which could succesfully be treated with polypyrrole. The lowest agarose content tested (0.050 wt %) still yielded strong adhering latex layers. Therefore, in the further synthesis of latex layers, latex suspensions with 0.05 wt % agarose were used.

As indicated in Example 2 below thick layers (ca. 5 $\mu$m) as well as thin layers (ca. 1 $\mu$m) were made. This was accomplished by using two different latex concentrations in the droplet that was cast on the electrode. The droplet size was kept constant. In both cases strong and smooth layers were obtained. Uniform spheres of two different dimensions were used to make latex membranes. Both particle sizes (112 and 220 nm diameter respectively) yielded layers with interspherical pores in the order of 50–200 nm.

The latex layers were modified with polypyrrole means of electrochemical polymerization. Although polymerization media having a prrole concentration of 0.2–0.8 Molar may be used. The polymerization medium was phosphate buffered saline (PBS), containing 0.3M pyrrole. This medium was chosen because enzyme treatment of the polypyrrole modified latex must preferably be performed in PBS. By using the same medium during polymerization and enzyme treatment it was avoided that exchange of dopant ions in the polymer with the solution could take place. When this would happen, major changes in the conducting polymer properties could occur. The electrochemical polymerization was galvanostatically controlled. In this way Applicant was able to vary the amount of polypyrrole in the latex layers by changing the polymerization time. It was found that galvanostatic polymerizaion gave much more reproducible results than polymerization under potentiostatic control. Potentiostatic control resulted in non-uniform coating of the latex layer; large areas on the electrode surface were still white (clean latex) while other areas showed spots of very high polypyrrole content. Galvanostatic polymerization at moderate current densities (20 mA/cm$^2$) resulted in an evenly spreaded polypyrrole coating of the latex.

The amount of charge (current*time) in the polymerization reaction was varied from 100 to 1000 mC/cm$^2$. The blackening of the originally white latex layers was proportional to the amount of charge passed. Although only qualitatively, this was a good indication of the proper galvanostatic polymerizaion of pyrrole in the matrix of latex particles.

Scanning electron microscopy (SEM) was used to image the coated latex layers. The images show how the membrane structure changes with polymerisation time (FIG. 2b–d). In FIG. 2b a very open structure is visible between the spheres that make up the bare latex layer. In FIG. 2c, the latex particles are coated with a thin layer of polypyrrole (amount of charge passed is 300 mC/cm$^2$). The porous structure is still present, while the internal surface now consists largely of polypyrrole. For reference, two uncoated latex spheres are visible at the surface. When the latex layer becomes coated with large amounts of polypyrrole, the porosity of the composite layer is lost (FIG. 2d). Shown in FIG. 2d is a thick latex layer, treated for 75 s. (1500 mC/cm$^2$). No enzyme electrodes could be made with these nonporous latices.

BRIEF DESCRIPTION OF THE DRAWINGS

FIG. 2(d): A layer as in FIG. 2(b), after treatment with polypyrrole for 75 seconds.

The numerals 1 to 5 indicate the following points:

(1): introduction of the polypyrrole-modified Nuclepore membrane (pore diameter: 800 nm; porosity: $3 \times 10^7$ pores/cm$^2$; material: polyester) obtained in accordance with the example below, the polypyrrole being provided with glucose oxidase, into an electrochemical cell, as described below for the test for determination of the enzyme activity;

(2): removal of the membrane from the electrochemical cell;

(3): introduction of the membrane into the electrochemical cell;

(4): removal of the membrane from the electrochemical cell;

(5): introduction of a solution which contains 0.02 U GOd in order to calibrate the measurement.

Figure 5:
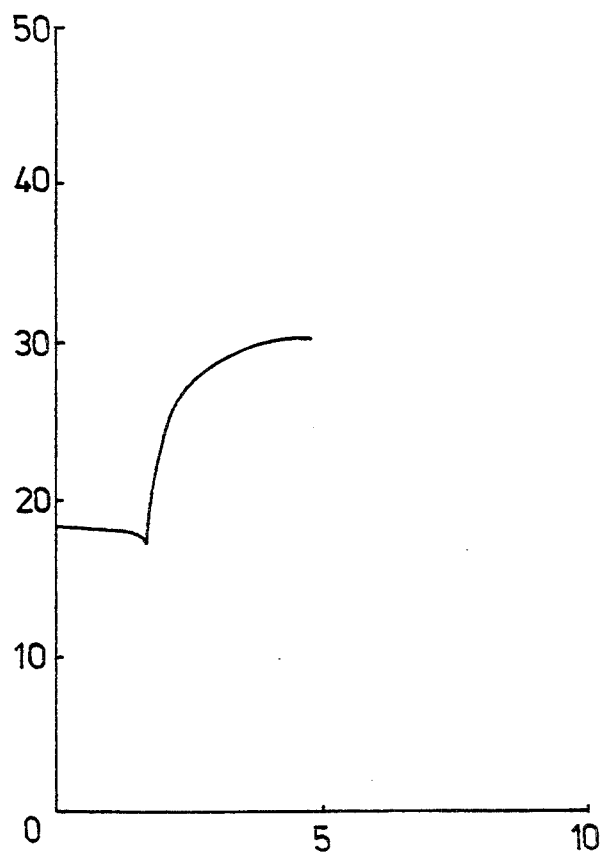

FIG. 5: Plot of the amperometric response with respect to glucose of a sensor membrane under an argon atmosphere. In the figure the time in minutes is plotted on the X axis and the current strength in microamperes on the Y axis.

Figure 6:
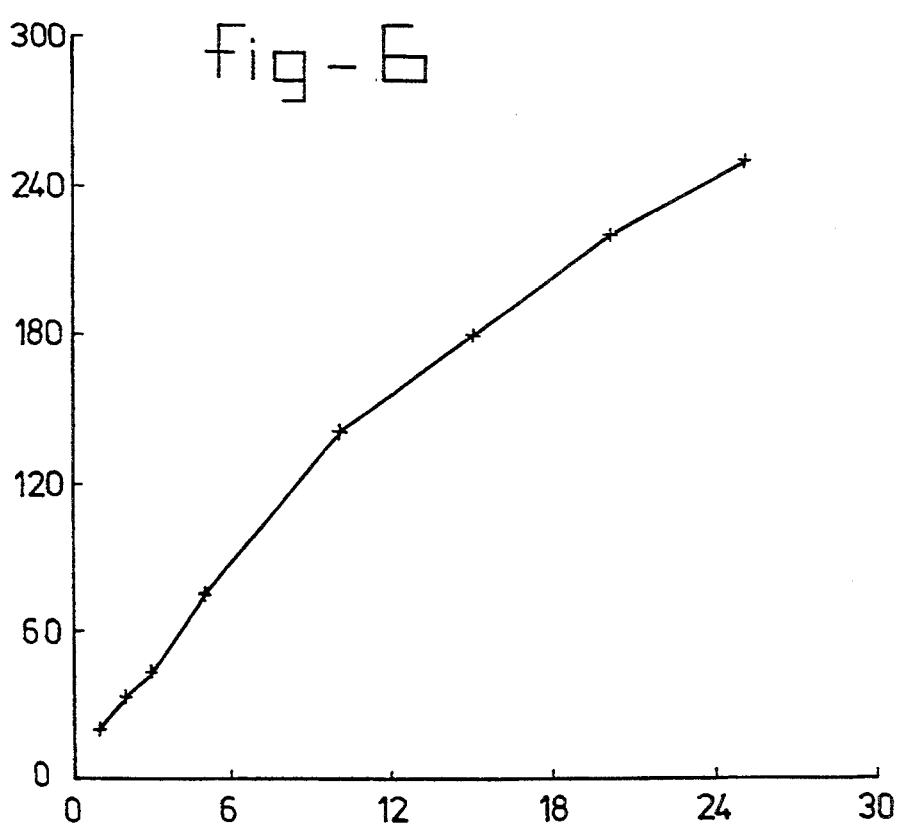

FIG. 6: Plot of the calibration curve for glucose. In this figure the glucose concentration in mM is plotted on the X axis and the current strength in microamperes on the Y axis. The curve shows the response under argon following injection of 15 µl, 30 µl, 45 µl, 75 µl, 150 µl, 225 µl, 300 µl and 375 µl of glucose (1M) in 15 ml of PBS buffer (pH=7.0; phosphate concentration: 10 mM).

Figure 7:
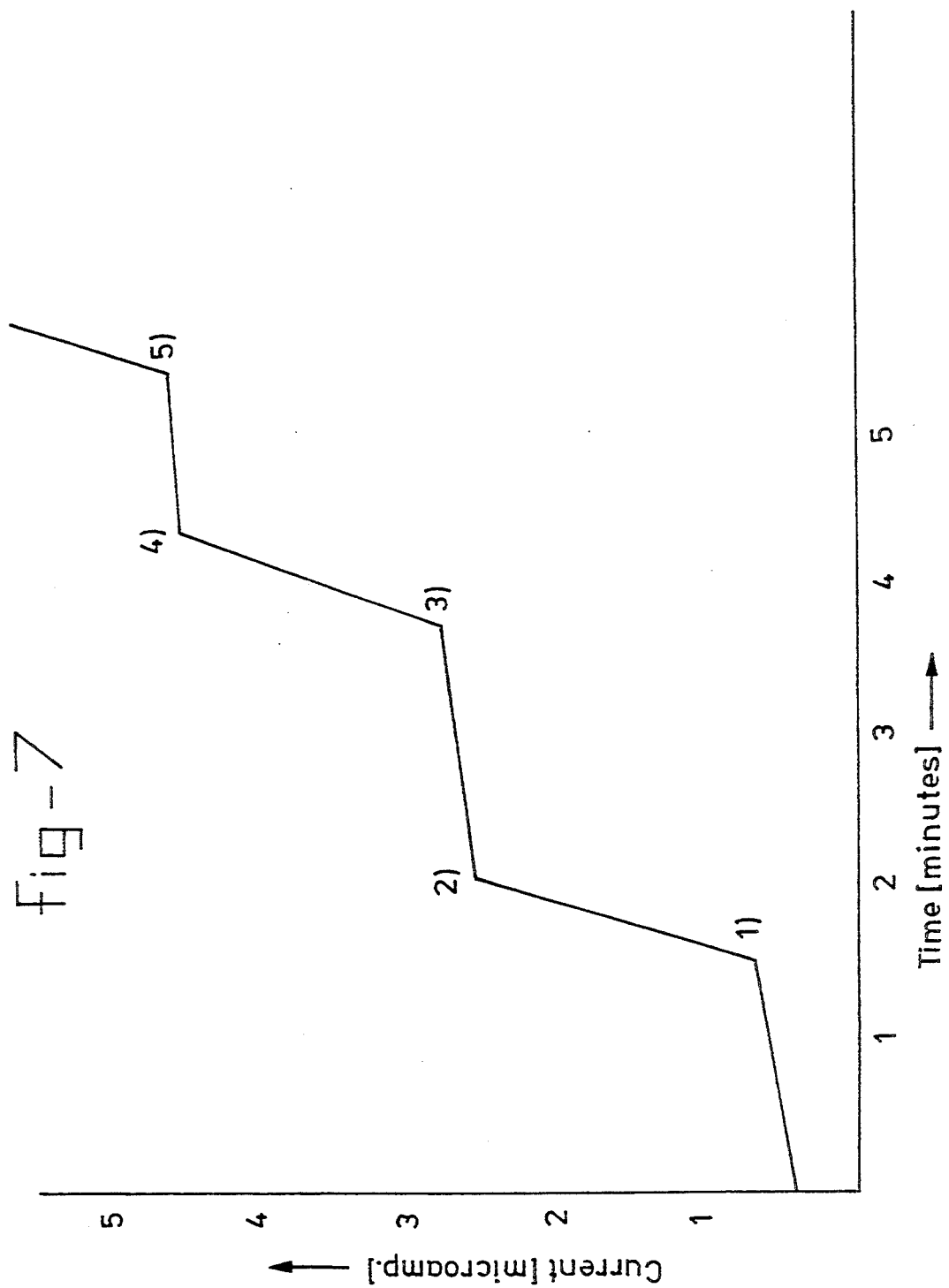

FIG. 7: Rotating disk electrode assay of glucose oxidase immobilized on 0.112 µm latex particles. (1) & (3): introduction of latex membrane electrode; (2) & (4): withdrawal of latex membrane electrode; (5): introduction of 0.125 U GOd.

Figure 8:
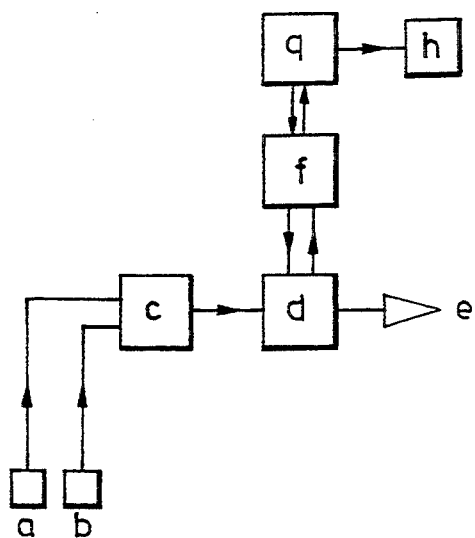

FIG. 8: Set up for continuous flow measurements of latex membrane biosensors. (a) carrier solution (PBS); (b) sample solution (glucose); (c) peristaltic pump; (d) flow cell; (e) waste; (f) potentiostat; (g) computer; (h) recorder.

Figure 9:
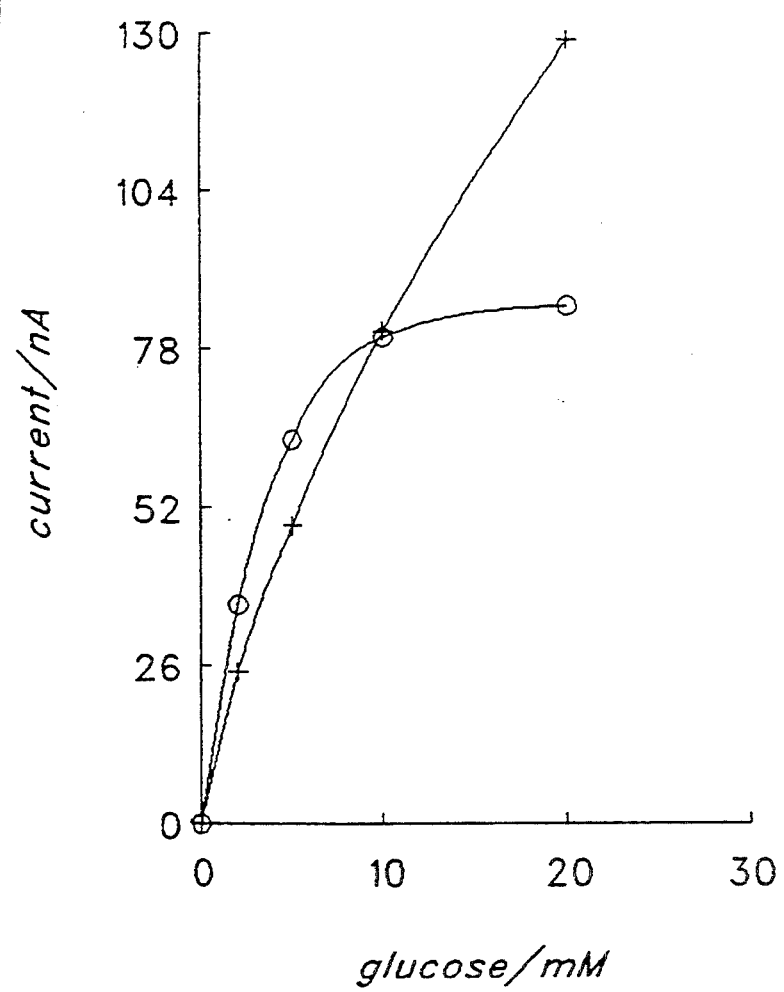

FIG. 9: Current response of thin latex layers (ca. 1 µm). Latex particle size 0.22 µm. Measured at 0.35 V vs. Ag/AgCl under argon atmosphere with 25 U/ml catalase. Membranes treated with various amounts of pyrrole polymerization charge. (+) 300 mC/cm$^2$; (o) 400 mC/cm$^2$.

Figure 10:
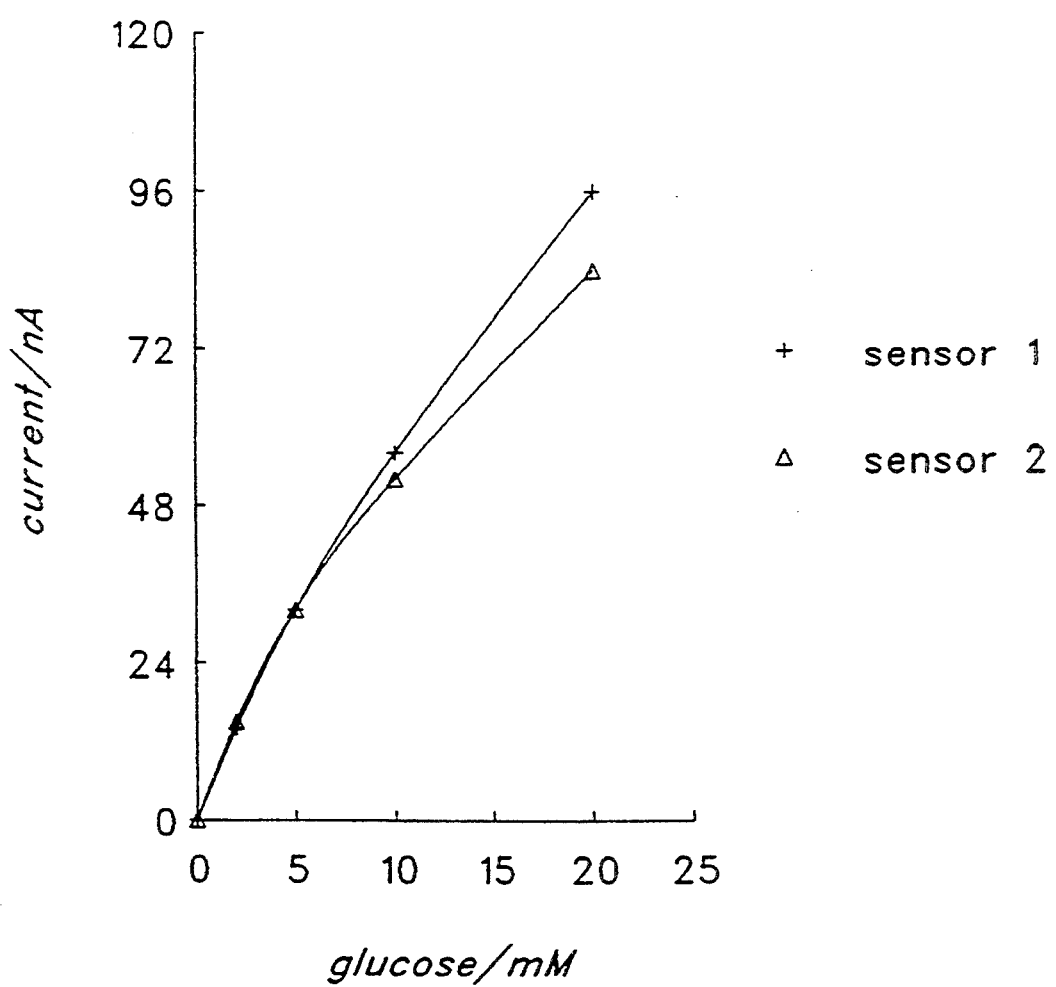

FIG. 10: Calibration curves for two latex glucose sensors, made under the same experimental conditions. Latex layer (ca. 1 µm) consisting of 0.22 µm particles. Measured at 0.35 V vs. Ag/AgCl under argon atmosphere with 25 U/ml catalase. Membranes treated with 150 mC/cm$^2$ of pyrrole polymerization charge.

Figure 11A:
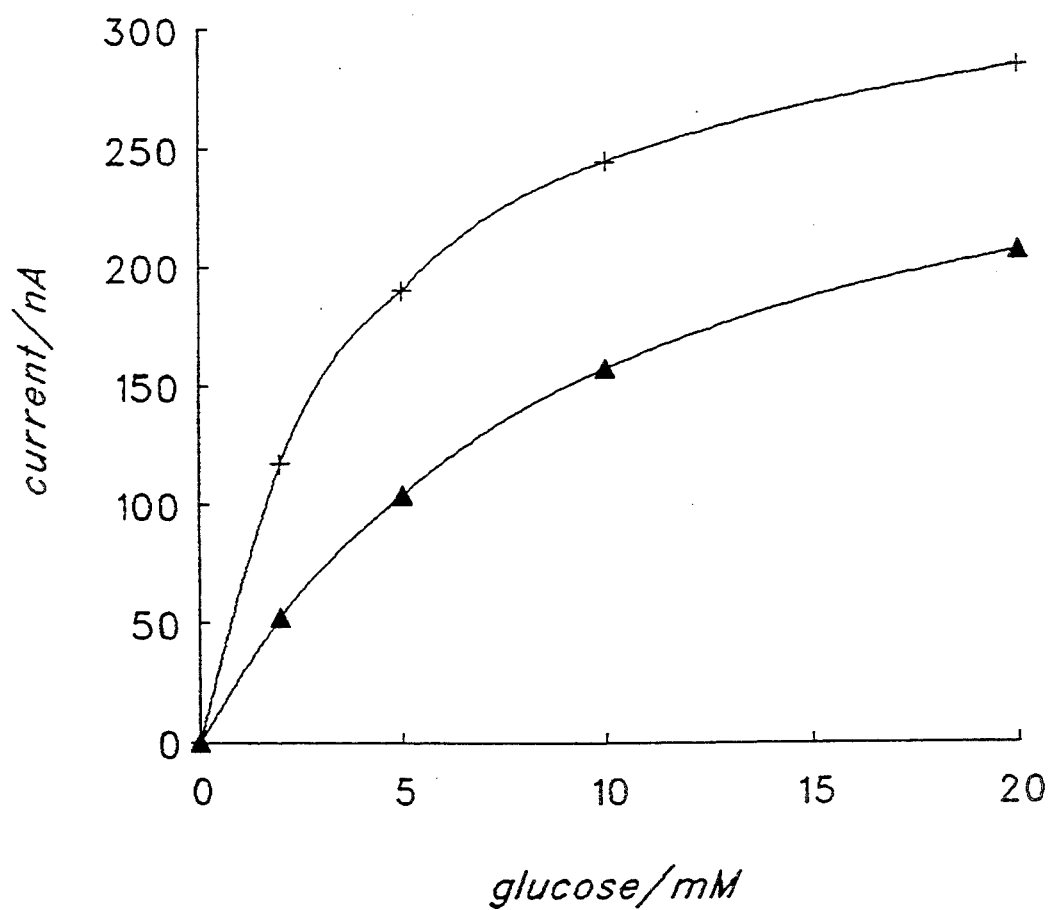
Figure 11B:
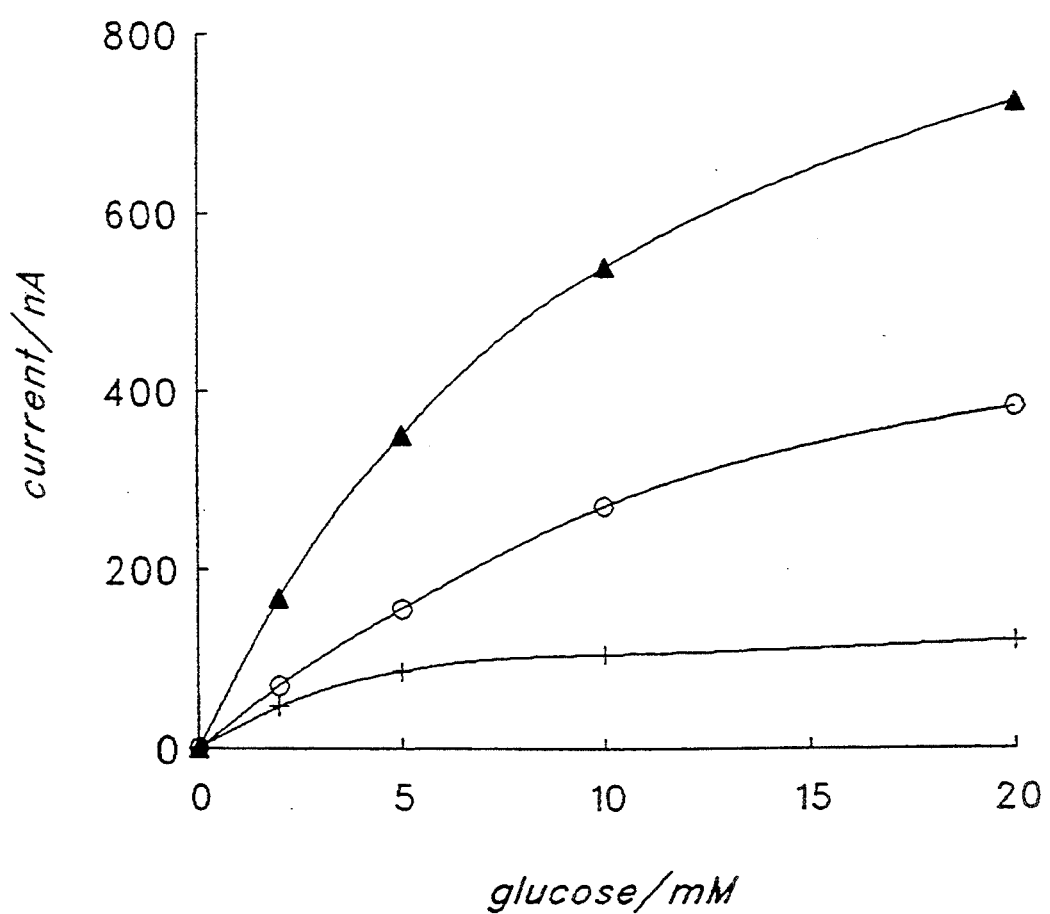

FIGS. 11(a) and 11(b): Current response of thick latex layers (ca. 5 µm). Measured at 0.35 V vs. Ag/Agcl under argon atmosphere with 25 U/ml catalase. Membranes of 112 and 220 nm particles, treated with various amounts of pyrrole polymerization charge.

11(a) 112 nm: (+) 200 mC/cm$^2$, (▲) 400 mC/cm$^2$;

11(b) 220 nm: (+) 200 mC/cm$^2$, (▲) 400 mC/cm$^2$, (o) 500 mC/cm$^2$.

Figure 12B:
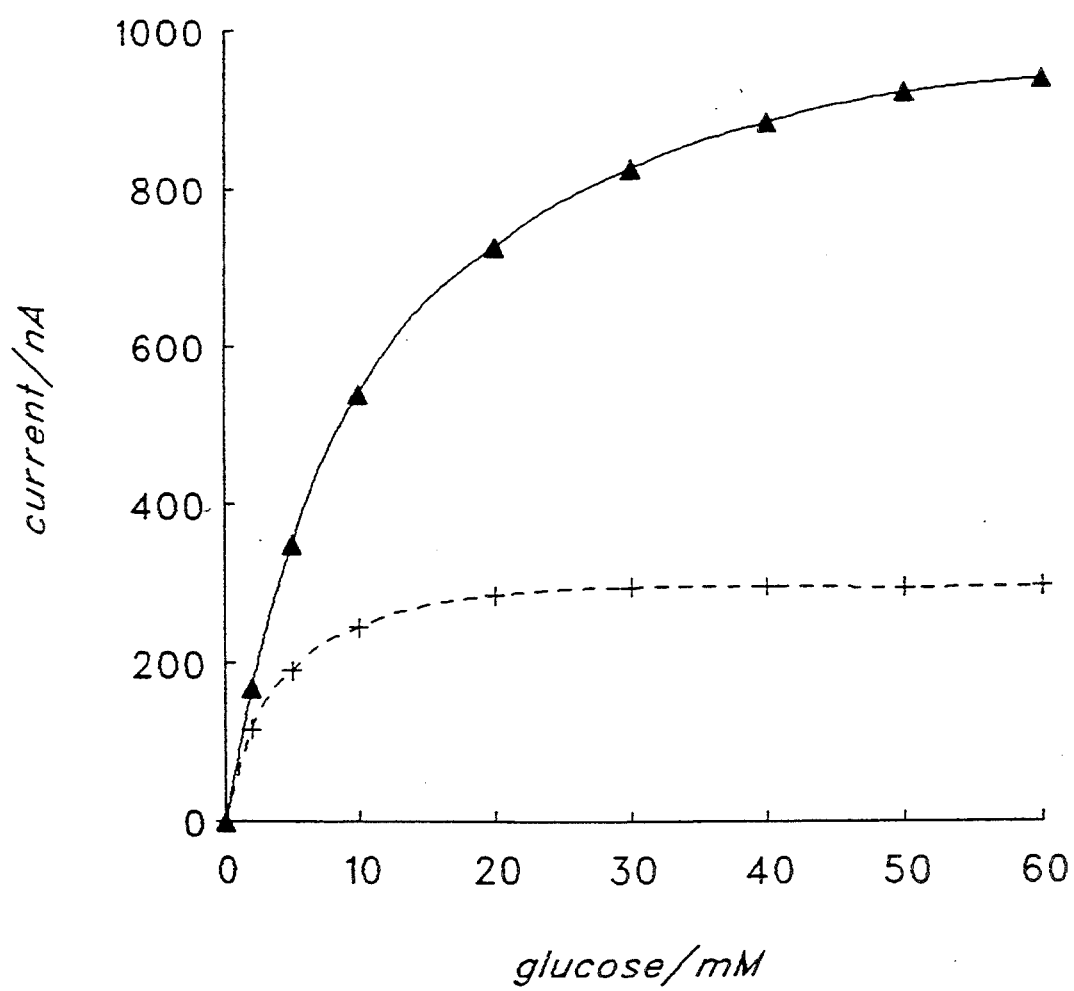

FIGS. 12(a) and 12(b): Calibration curves for optimized latex-polypyrrole sensors. Measured at 0.35 V vs. Ag/Agcl under argon atmosphere with 25 U/ml catalase.

12(a) Thin layer of 220 nm latex particles, charge 150 mC/cm$^2$;

12(b) Thick layer of latex: (+) 112 nm latex, charge 200 mC/cm$^2$; (▲) 220 nm latex, charge 400 mC/cm$^2$.

Figure 13:
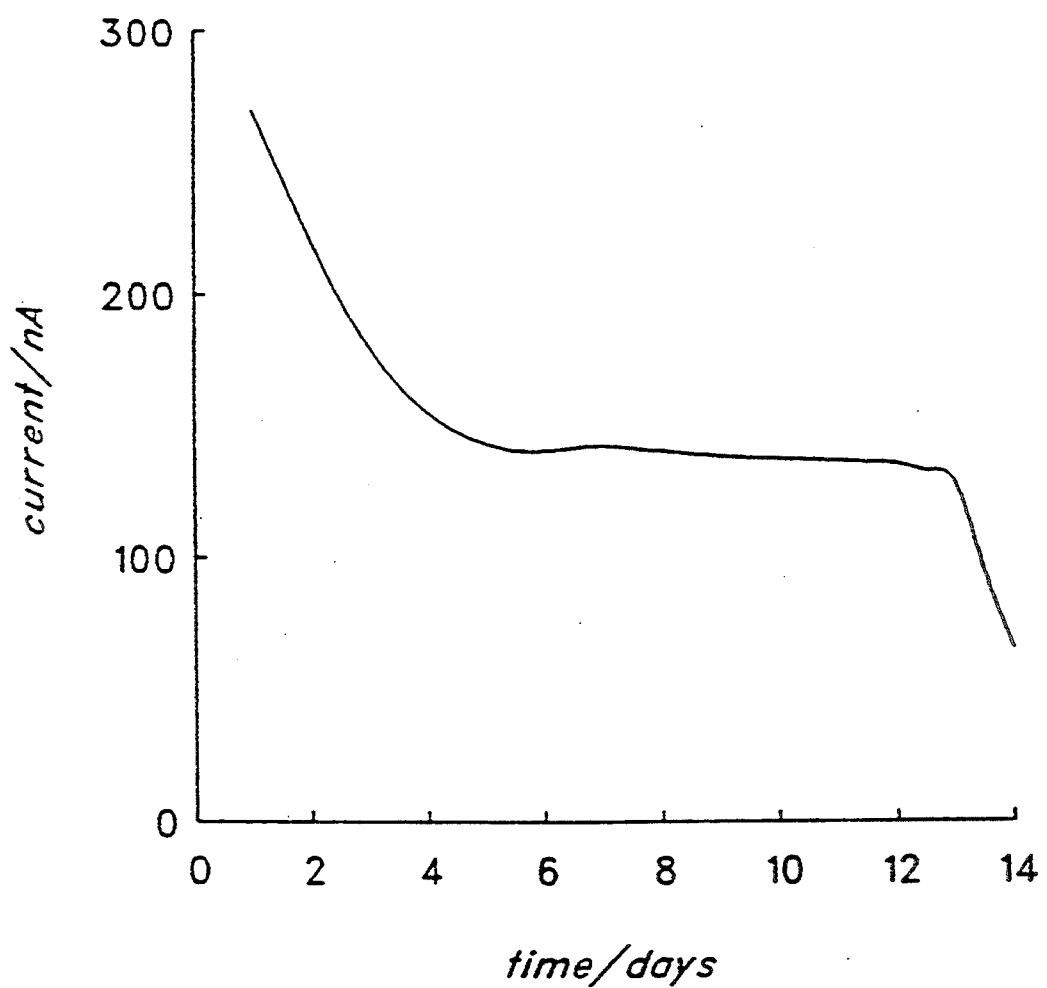

FIG. 13: Stability of latex-polypyrrole biosensor at continuous operation under ambient atmosphere in the presence of 1 mM glucose. The activity was measured daily by introducing an additional amount of glucose up to a concentration of 5 mM.

Figure 14:
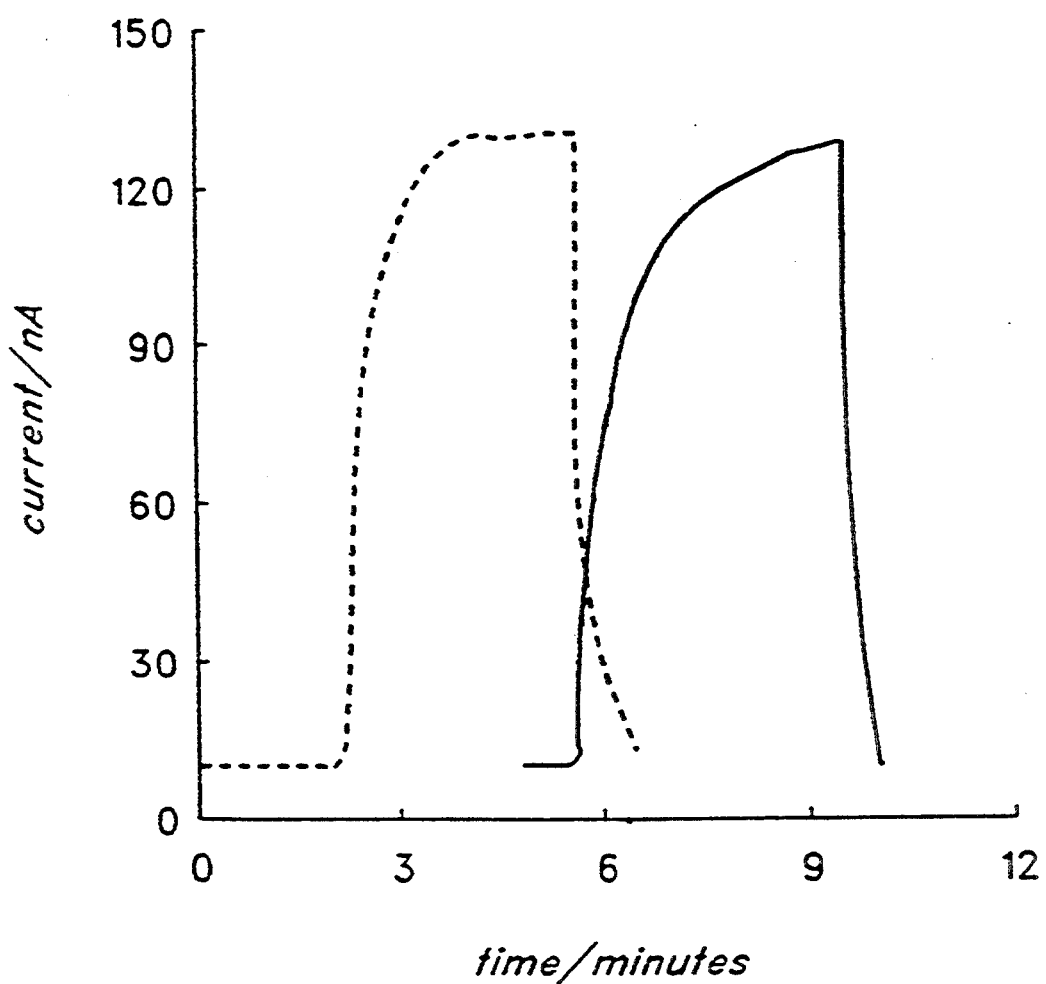

FIG. 14: Current response of a latex-polypyrrole biosensor upon the addition of glucose. Measurement at 0.35 V vs. Ag/AgCl. Dashed line: in air saturated solution under ambient atmosphere; solid line: in argon flushed solution under argon atmosphere with 25 U/ml catalase.

Figure 15:
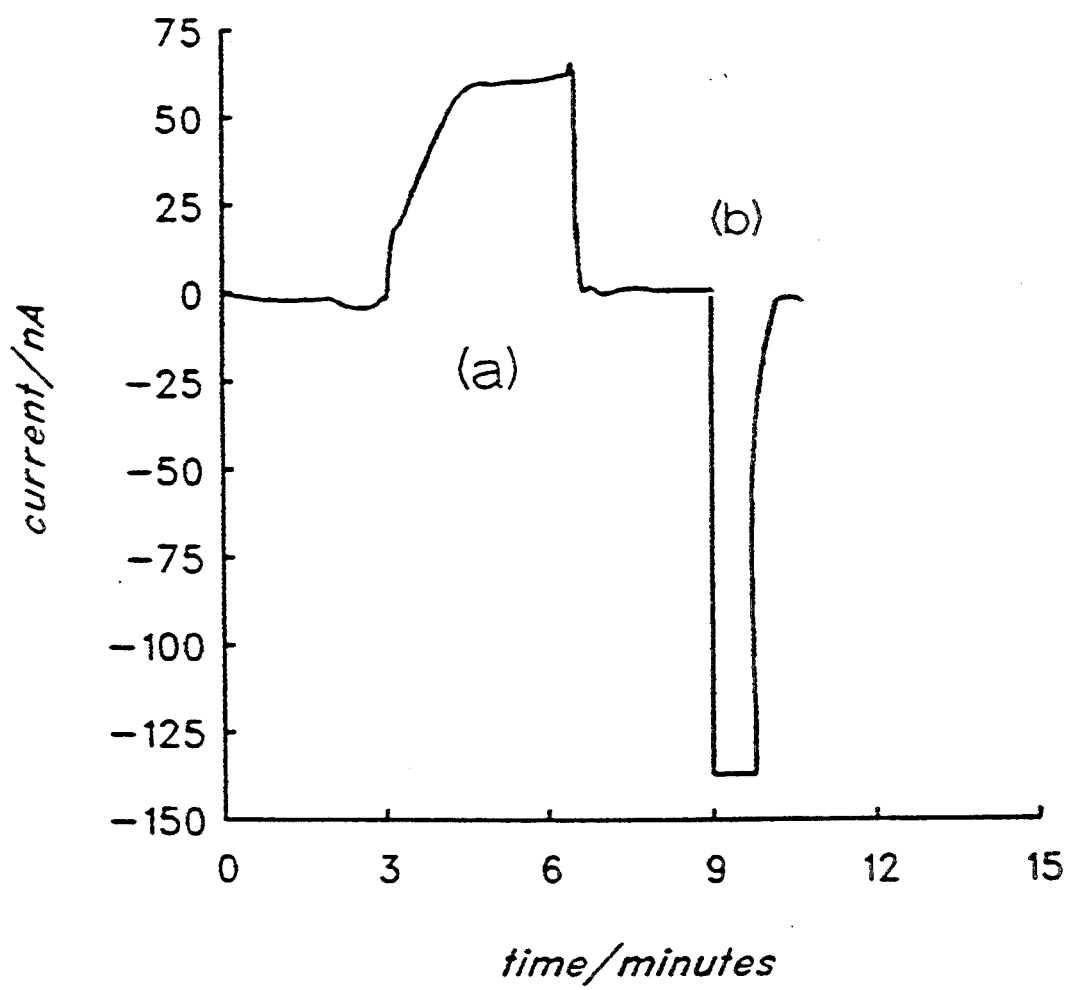

FIG. 15: Current response versus time of a latex membrane consisting of 220 nm particles with 100 mC polypyrrole. Measuring potential 0.10 V vs. Ag/AgCl.

(a) 10 mM glucose under ambient atmosphere;

(b) 0.0025% hydrogen peroxide.

EXAMPLE I

A) Production of an Electrode According to the Invention (1) Reagents Used

Glucose oxidase (E.C. 1.1.3.4) from *Aspergillus niger*, type II (25,000 U/g), and catalase (E.C. 1.11.1.6) from bovine liver, 2800 U/mg were obtained from Sigma. Benzoquinone was obtained from Aldrich (France) and was sublimed before use. Pyrrole was obtained from Merck and anhydrous iron(III) chloride (98%) was obtained from Fluka and these compounds were used in the form supplied. The Nuclepore membranes were obtained from Ankersmit (The Netherlands). All other reagents used were of p.a. grade (analytical grade).

(2) Oxidising Chemical Polymerisation of Pyrrole in the Nuclepore Membranes

Figure 1:
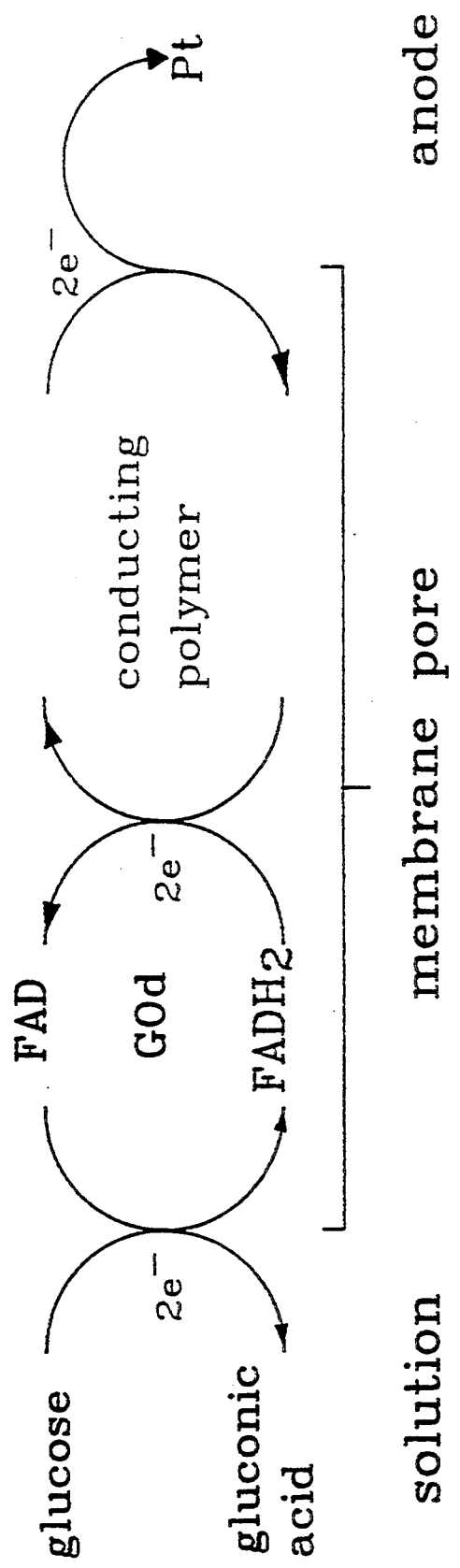
FIG. 1: Electron shuttle showing the path of the electrons involved in the enzymatic glucose oxidation.
Figure 2A:
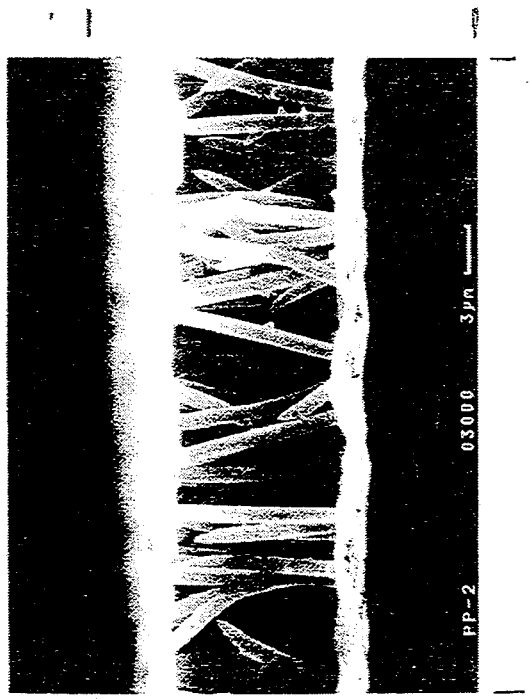
FIG. 2(a): Track-etched Cyclopore membrane coated with a conducting polymer of polypyrrole in which small hollow channels are formed during the polymerization process.
Figure 2B:
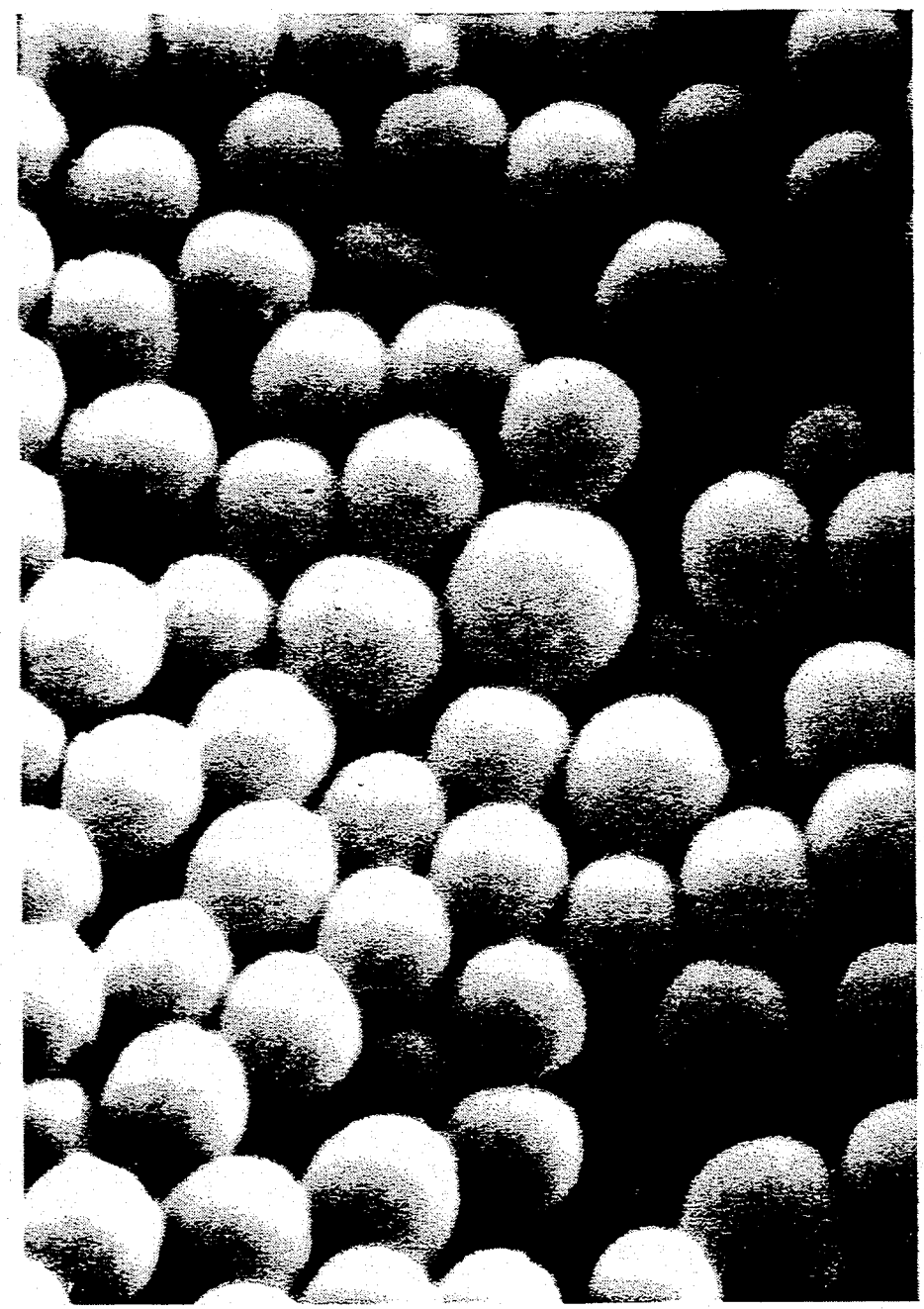
FIG. 2(b): An untreated layer of 0.22 $\mu$m latex particles on platinum electrode.
Figure 2C:
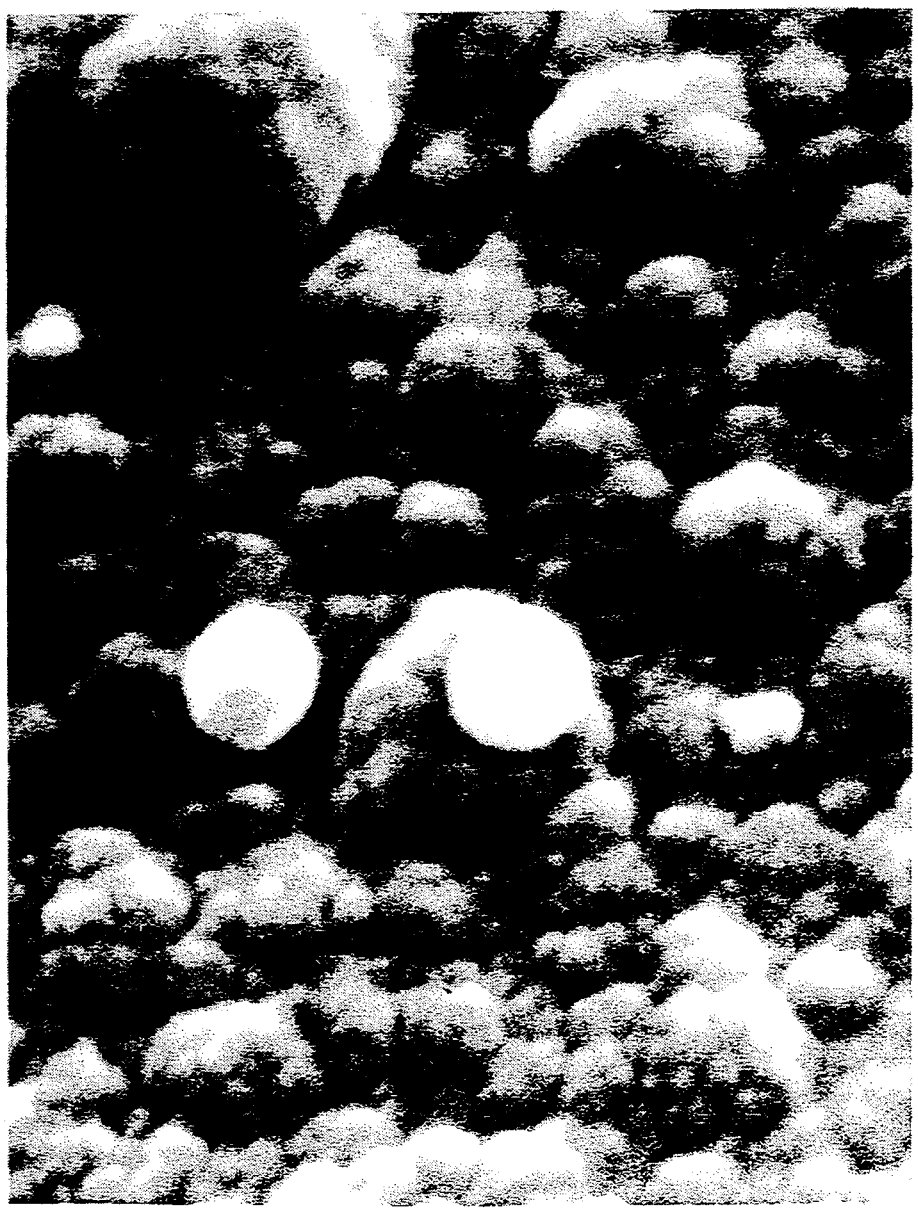
FIG. 2(c): A layer as in FIG. 2(b), after treatment with polypyrrole for 15 seconds.
Figure 3:
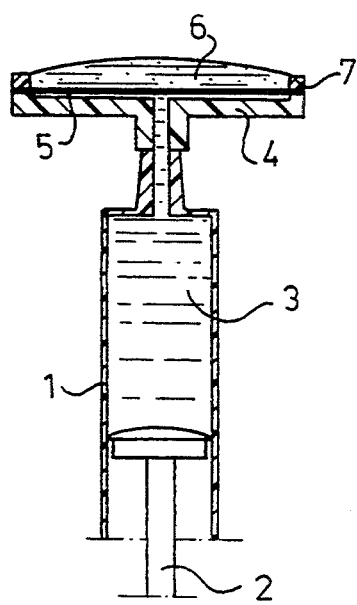
FIG. 3: Set-up for carrying out the pyrrole polymerisation in the pores of a membrane:
(1) injection syringe;
(2) plunger of the injection syringe;
(3) FeCl$_3$ solution;
(4) holder for the membrane;
(5) membrane;
(6) pyrrole solution;
(7) rubber ring.

The polymerisation of pyrrole in the pores of the filtration membranes of the Nuclepore type was achieved by allowing an aqueous 2M FeCl$_3$ solution (amount usually used: 4 ml) and an aqueous 0.6M pyrrole solution (amount usually used: 1 ml) to precipitate in a membrane (diameter: 25 mm). In practice, this was carried out by positioning an injection syringe, which was filled with the iron chloride solution, vertically and mounting a standard membrane holder on the syringe (see FIG. 3). The level of oxidizing iron(III) chloride solution in the membrane holder was raised until the solution just touched the membrane resting on the said holder. The memrane was weighted down with a rubber ring. 1 ml of the abovementioned pyrrole solution was then applied to the membrane. The polymerisation time was measured from the time this solution was applied. For Nuclepore membranes containing pores having a diameter of 0.8 µm (pore density: $3 \times 10^7$ pores/cm$^2$) and containing pores having a diameter of 1 µm (pore density: $2 \times 10^7$ pores/cm$^2$) the polymerisation was continued for 1–10 min., after which time the membrane was removed and rinsed with excess water or a phosphate buffer (PBS); pH=6.5.

Coating of One Side of the Nuclepore/Pyrrole Membrane According to (2) with Platinum Using a template with an opening which was just a little smaller than the diameter of the membrane concerned, a polypyrrole-modified filter membrane was pressed against the cooling plate of an Edwards S150B sputtercoater. 100–400 nm of Pt were then applied by sputtering under an argon pressure of 8 nBar and using a sputtering current of 50 mA. The layer thickness was measured using an Edwards FTM5 unit.

Immobilisation of Glucose Oxidase in the Modified Filter Membranes According to (3)

For enzyme immobilisation, the membranes which were obtained in accordance with (3) and had an original pore diameter of 800 and 1000 nm were used. For immobilisation, a membrane was introduced into 4 ml of a 5 mg/ml GOd solution, after which the whole was shaken with the aid of a Gyratory Shaker Model G2 (New Brunswick Scientific, USA). The immobilisation took place at 4° C. over a minimum of half an hour. The membrane was then rinsed in PBS (pH=6.5) and dried overnight at 4° C. This drying took place in a desiccator under normal pressure and in the presence of $CaCl_2$.

Testing of the Electrode According to the Invention Obtained Under (A)

Test Methods (1)

The enzyme activity was determined with the aid of the three-electrode cell which contained 15 ml of 0.1M phosphate buffer (pH=6.5), 5 mM benzoquinone and 0.5M glucose. The glucose solution was allowed to mutarotate for at least 24 hours. The test was carried out using a Pt rotary disc electrode (RDE), which was provided with an Electrocraft Corporation Model E550 motor and an E552 speed control unit. A potential of 0.350 V ($Ag/Ag^+$ reference) was applied to Pt working electrode and the latter was rotated at a speed of 3000 revolutions per minute. A spiral-shaped Pt electrode was used as auxiliary electrode. the solution was flushed with argon before each test. During the test the solution was blanketed with argon.

All electrochemical measurements were carried out using an Autolab potentiostat which was controlled by means of an Olivetti M24 personal computer and General Purpose Electrochemical System (GPES) software (Eco Chemie, The Netherlands). The current output was recorded using a Yew 3056 pen recorder. The actual test was carried out by recording the current output of the RDE on submerging the sample membrane in the abovementioned solution.

(2)

Amperometric measurements on membrane sensors according to the invention were carried out in a three-electrode cell using the sensor as working electrode. In this case the membrane was clamped between a folded Pt strip, which strip was electrically connected to a potentiostat. In order to obtain a rigid electrode, the membrane was joined to a glass plate with the aid of double-side adhesive tape.

A potential of 0.175 V against Ag reference was applied to the sensor. A spiral-shaped Pt wire was used as auxiliary electrode. The cell contained 15 ml of 0.1M phosphate buffer (pH=6.5) containing 10 U/ml catalase and was kept under an argon atmosphere. Stirring was carried out with the aid of a magnetic rod stirrer. Following an initial current strength this fell to a steady state value, after which samples of 1M glucose solution were added; the resulting current response was recorded.

Figure 4:
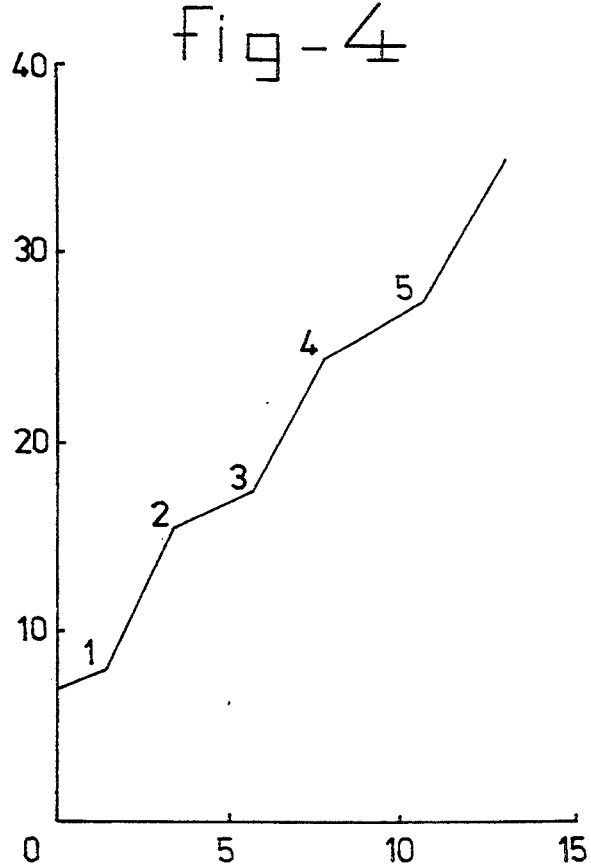
FIG. 4: Plot of GOd activity of polypyrrole-modified Nuclepore membrane, the polypyrrole being provided with glucose oxidase. In this figure the time in minutes is plotted on the X axis and the current strength in microamperes on the Y axis.

C) Results (1)

the enzyme activity was determined with the aid of the above method. When carrying out the test, the natural co-substrate (oxygen) was replaced by the synthetic electron accepto benzoquinone. The hydroquinone, which was formed during the catalytic cycle, was measured eletrochemically using the rotary disc eletrode (RDE). The regeneration of the benzoquinone from hydroquinone starts at the RDE at a certain potential (0.35 V against Ag) and the resulting current is a measure for the enzyme activity. Although a slight increase in current strength arises as a consequence of the non-catalysed oxidation of glucose by benzoquinone, the current strength as a consequence of the catalytic action of the enzyme is sufficiently large to give an appreciable difference in the gradient of the current-/time curve (see FIG. 4). FIG. 4 shows the effect on the measured current when the membrane according to the invention (see above) is introduced into the electrochemical cell. As can be seen from FIG. 4, the current increases immediately following the introduction of the membrane. This effect occurs in the case of the Nuclepore membranes having initial pore diameters of 800 nm and 1000 nm, which have been indicated above.

The fact that the activity returns to the initial value following removal of the membrane according to the invention is evidence of suitable immobilisation of the enzyme. Material which is not correctly immobilised will remain in the solution and have the consequence that the gradient of the line after point 2 in FIG. 4 would be higher. This has in fact also been found in the case of membrane which were treated with a GOd solution but did not have a polypyrole coating in the pores of the membrane. Since no polypyrrole is present on the surface of the membrane (see the experimental section), it is assumed that no enzyme is absorbed on this surface. FIG. 4 shows that the successive introduction and removal of the membrane has no influence on the amount of activity immobilised enzyme. This is also the case if a membrane is measured which has been stored for two weeks at 4° C. No significant decrease in the enzyme activity can be detected. At the end of each measurement, a known amount (5 μg=0.1 U) of enzyme is added in order to calibrate the activity (point 5 in FIG. 4). Assuming that the electrochemical reaction is a rapid process, the diffusion of hydroquinone to the electrode will be the rate-determining step. Therefore, it is of little or no significant for the measurement where the hydroquinone is formed. This signifies that the gradients resulting from immobilised and free enzyme can be correlated, at least in a semi-qualitative manner. It can be concluded from the calibration that about 0.02 $U/cm^2$ of active GOd is present in the membrane.

(2)

FIG. 5 shows the electrochemical response of the system with respect to the addition of glucose. In this example, as indicated above, the membrane was used as working electrode. A potential of 0.175 V against Ag was applied to the membrane. A platinum wire served as auxiliary electrode. The amperometric response was determined in a stirred cell, which was filled with 15 ml of 0.1M phosphate buffer. The Nuclepore membranes containing pores having a diameter of 800 and 1000 nm, which have been described above, were tested in this way. The increase in current strength (FIG. 5) was determined under an argon atmosphere and in the presence of 10 U/ml catalase. The latter enzyme was added for the decomposition of any $H_2O_2$ which may be produced enzymatically to accidental oxygen mediation. The potential applied was, as stated, 0.175 V against Ag reference, which is too low a potential to oxidise $H_2O_2$. Therefore, it can be stated that the enzyme transports its electrons directly to the conducting polymer. The delimited space in the pores of the membrane, together with the amorphous structure of the polypyrrole, apparently brings the active centres of the enzyme molecules into close contact with the conducting polymer.

The response time is less than one minute, which can be regarded as rapid taking into account the geometry of the sensor. The time which is needed to obtain a uniform glucose concentration throughout the entire solution must also be taken into account here; this time can be 10 seconds or more.

The injection of large amounts of glucose gives rise to a saturation effect, so that the current response is not linear with the glucose concentration. This became clear when a calibration curve was made by the successive addition of specific amounts of glucose to the same solution in the cell (FIG. 6). Measurements carried out under argon in the presence of cataslase in the solution gave good results up to a concentration of 25 mM glucose.

(3) Competition Between the Conducting Polymer and Oxygen

When oxygen is present, it becomes a competing substrate for the polypyrrole in respect of the acceptance of electrons from the flavin units of GOd. In this case, not only does the current become smaller because of the direct electron transfer to the polymer but hydrogen peroxide is also formed. Apart from the fact that hydrogen peroxide degrades the enzyme and the conducting polymer, this compound also contributes to the measured signal. Despite the low potential applied to the working electrode (0.175 V/Ag), the latter still reacts to hydrogen peroxide. However, in the presence of catalase, the $H_2O_2$ formed is effectively destroyed and the measurement is not disturbed.

In order to obtain some insight into the effects of catalase and the presence of an inert atmosphere, measurements were carried out under various test conditions. The results are given in Table A below.

TABLE A

Response for glucose under various test conditions

| Test conditions | Response [$\mu A$] |
| --- | --- |
| Air/PBS buffer only | 95 |
| Air/20 U catalase | 85 |
| Air/180 U catalase | 85 |
| Argon/180 U catalase | 85 |

(The response relates to 75 $\mu l$ of glucose (1M) injected into a 15 ml PBS solution (pH = 6.5)).

It can be seem from the results given in Table A that a small amount of catalase already suppresses the interference of oxygen, while argon had no additional effect.

(4) Selectivity

The selectivity of the sensor according to the invention was tested for fructose. No response for fructose was detected.

EXAMPLE II

A) Production of an Electrode According to the Invention (1) Materials and Apparatus Glucose oxidase (E.C. 1.1.3.4) type II (25,000 U/g) from Aspergillus niger and catalase (E.C. 1.11.1.6, 2800 U/mg) from Bovine liver were obtained from Sigma. Benzoquinone was from Aldrich (FRG) and was sublimed prior to use. Pyrrole was from Merck and was distilled before use. Latex suspensions with particles of 112 and 220 nm were from Perstorp analytical. Agarose type VII was purchased from Sigma. All other reagents were of analytical grade.

The used galvanostat was constructed at the University of Nijmegen, The Netherlands. The current output of the galvanostat was monitored with a Fluke 45 digital multimeter. All electrochemical measurements were performed with an Autolab potentiostat controlled by an Olivetti M24 Personal Computer and General Purpose Electrochemical System (GPES)-software (Eco Chemie, Utrecht, The Netherlands). Current output was recorded on a Yew 3056 pen recorder. Electron micrographs were made on a CAMSCAN scanning electron microscope (Cambridge Instruments).

(2) Coating with a Metal Layer

Glassy carbon disks of 8 mm diameter (Antec, Leiden, The Netherlands) were used as the base electrode. The electrodes were polished with Alpha Micropolish Alumina No. 1C (1.0 micron, Buehler LTD., U.S.A.). Platinum was applied on the polished surface with an Edwards sputtercoat S150B. A platinum target of 8 cm diameter and 0.5 mm thickness was used as the platinum source. The layer thickness was monitored with an Edwards FTM5 unit. Sputtering was continued until the thickness of the platinum layers was 300 nm.

(3) Preparation of Latex Layers

Agarose type VII was dissolved by boiling an appropriate amount (0.1 or 0.25 wt %) for 2 minutes in distilled water. Freshly made solutions, which were still hot, were used to make the latex membranes. A volume of agarose solution was mixed thoroughly with an equal volume of latex suspension. A 75 $\mu l$ droplet was applied on a freshly sputtered platinum disk. After application, the electrode was put in the refrigerator overnight. The dried latex electrode was put in an oven at 333° K. for 1 hour.

(4) Preparation of Latex Membranes with Polypyrrole

Latex electrodes were sealed with teflon tape in such a way as to leave only the latex surface for making contact with the polymerization medium. An aqueous solution containing 0.9% potassium chloride and 10 mM phosphate (PBS), together with 0.3M pyrrole was used in the polymerization reaction. The latex layer was put in the solution at least one minute before polymerization took place to allow the solution to penetrate the membrane sufficiently. Afterwards, a constant current (20 mA/cm$^2$) was supplied to the cell for an appropriate time (see Table B). A platinum plate acted as counter electrode. When polymerization was finished the electrodes were rinsed with PBS.

(5) Immobilization of the Enzyme

Enzyme immobilization was achieved by agitating (Gyrotory Shaker model G2, New Brunswick Scientific, USA) membranes in 3 mL of 5 mg/mL of GOd at a temperature of 227° K. for 4 hours. The membranes were successively dried overnight on $CaCl_2$ in a desiccator.

B) Testing of the Electrode According to the Invention Obtained Under (A)

(1) Enzyme Activity Assay

Enzyme activity was assayed with a three electrode cell containing 20 mL phosphate buffered saline (PBS), pH 7.5, 5 mM benzoquinone and 0.5M glucose. Prior to use, the glucose solution was allowed to mutarotate for at least 24 hours. The assay was performed with a platinum rotating disk electrode (6 mm diameter) equipped with an Electrocraft corporation model E550 motor and E552 speed control unit. The platinum working electrode was set at a potential of 0.350 V (Ag/AgCl reference) and was rotated at a speed of 2000 rpm. A platinum wire was used as auxiliary electrode. The solution was flushed with argon before each experiment. During the assay argon was blanketed over the solution.

The actual assay was performed by monitoring the current output of the RDE while immersing a sample membrane into the solution. The enzymatic activity of the various latex-polypyrrole membranes are indicated in Table B.

TABLE B

| Charge (mC/cm$^2$) | 1 μm thickness | | 5 μm thickness | |
|---|---|---|---|---|
| | 112 nm | 220 nm | 112 nm | 220 nm |
| 100 | + | + | x | x |
| 150 | + | + | x | x |
| 200 | + | + | + | + |
| 300 | + | + | + | + |
| 400 | − | + | + | + |
| 500 | − | − | + | + |
| 1000 | − | − | − | − |

+: enzymatically active membranes
−: non-active membranes
x: not tested

(2) Amperometric Biosensor Activity Measurements

To perform amperometric measurements, the enzyme membrane was placed as working electrode in a three electrode flow cell (Sparc Holland). To insulate the active surface of the membrane from the auxiliary electrode, it was covered with a teflon spacer of 1 mm thickness. In the spacer a duct of approximately 0.15 cm$^2$ was left, allowing the membrane to make contact with the solution. An Ag/AgCl electrode was used as reference electrode. The base of the flow cell acted as auxiliary electrode (glassy carbon). Buffer solution was driven through the cell at a rate of 1.75 ml/minute (Watson Marlowe 101U peristaltic pump). The potential of the membrane was set at 0.350 V. When the background current had been diminished sufficiently, the buffer solution was replaced by the glucose solution and the current response was monitored, see Table C.

TABLE C

| Charge (mC/cm$^2$) | 1 μm thickness | | 5 μm thickness | |
|---|---|---|---|---|
| | 112 nm | 220 nm | 112 nm | 220 nm |
| 100 | 12 | 12 | x | x |
| 150 | 20 | 20 | x | x |
| 200 | 20 | 25 | 40 | 25 |
| 300 | 30 | 30 | 70 | 50 |
| 400 | − | 50 | 70 | 60 |
| 500 | − | − | 95 | 85 |

−: no enzyme activity
x: not tested

C) Results (1)

As indicated under (A) an enzyme electrode was constructed from the modified latex layer by treating it with glucose oxidase. Immobilization of glucose oxidase inside the latex-polypyrrole pore structure was achieved by agitating a modified electrode in an aqueous solution (PBS), containing the enzyme, for 4 hours and successively drying overnight. The immobilization procedure was conducted at a temperature of 277° K.

The enzyme electrodes were tested separately (viz. independent of the biosensor activity) for enzymatic activity by means of the Enzyme activity assay, described earlier. In this way, the natural cosubstrate (oxygen) was replaced by the artificial electron acceptor benzoquinone. Hydroquinone, which is formed in the catalytic cycle, was measured electrochemically at a rotating disk electrode (RDE). The regeneration of benzoquinone from hydroquinone takes place at a fixed otential (0.35 V vs. Ag/AgCl). The resulting current is a measure of the enzymatic activity. Although there is a slight raise in current caused by the spontaneous oxidation of glucose by benzoquinone, the raise in current as a result of the catalytic action of the enzyme is large enough to give a significant difference in slope of the current-time plot.

In FIG. 7 the effect on the measured current is shown when a GOd treated polypyrrole-latex membrane with originally 112 nm spheres, is introduced into the electrochemical cell. This latex membrane was treated with an amount of polypyrrole corresponding to 100 mC/cm$^2$. As can be seen, the current increases immediately after introduction of the membrane. Membranes with 220 nm spheres also showed this behaviour. The fact that after withdrawal of the membrane the activity returns to its initial value, is an indication that the enzyme is properly immobilized. Not properly immobilized material would stay in solution and the slope of the line after point 2 in the figure would be higher. This assay showed that drying of the membrane after adsorption of the enzyme is essential. Enzyme was washed out completely when membranes were tested for activity directly after enzyme treatment.

It can be concluded from the assay that adsorption of glucose oxidase to the polypyrrole surface inside the porous latex matrix, followed by drying results in proper immobilization of the enzyme with retention of enzymatic activity.

A number of enzyme electrodes based on latex and polypyrrole were tested for enzymatic activity with this assay. In Table B the results are listed for various latex membranes composed of either 112 or 220 nm spheres, containing increasing amounts of polypyrrole. The polypyrrole content is represented by the amount of charge passed in the electrochemical polymerization. It can be seen in Table B that up to a certain amount of charge enzymatically active layers are yielded after enzyme treatment. Furthermore, the activity depends on the layer thickness of the latex membranes and not on the size of the particles (i.e. when particles of 112 and 220 nm are compared). The thick layers were able to accomodate more polypyrrole before they became unfit for enzyme immobilization. This was to be expected because thicker layers contain more interspherical space than thin layers. Physical adsorption is used to immobilize the enzyme. Therefore, monolayer coverage of the polypyrrole surface is assumed. Thick latex layers contain more polypyrrole surface. Consequently, higher enzyme loading is expected. The independence of particle size probably comes from the fact that both particle sizes give rise to interspherical pores of approximately identical dimensions.

(2) Amperometric Latex-Polypyrrole Biosensors

In order to measure the biosensor activity of the enzyme treated latex-polypyrrole membranes, they were placed as the working electrode in an amperometric three electrode cel. The cell was part of a continuous flow system (FIG. 8), which made it feasible to switch between a buffer solution and a solution that contained the enzyme substrate, glucose. All experiments were conducted under an argon atmosphere and 25 U/ml catalase present in all solutions. Catalase was added to eliminate any enzymatically produced $H_2O_2$.

Except for some boundary cases, only the electrodes which showed enzymatic activity in the rotating disk electrode assay were tested as a biosensor. This means that electrodes containing thin latex layers and amounts of polypyrrole corresponding to more than 400 $mC/cm^2$ were not tested (Table B, columns 2,3). Thick latex layers, treated with 1000 $mC/cm^2$ or more were also not measured as a biosensor (Table B, columns 4,5). The boundary cases were, as visible in Table B, 400 and 500 $mC/cm^2$ for thin and thick layers respectively.

The current response of the different biosensors was tested by measuring various glucose concentrations with the individual enzyme treated latex-polypyrrole electrodes. Unless stated otherwise, the amperometric measurements were performed at a potential of 0.35 V versus Ag/AgCl. The polypyrrole-latex membranes were cast on platinum. Non-specific electrochemical glucose oxidation at the platinum surface could accidentlly occur. Therefore, the electrodes were also tested for glucose sensitivity before they had been treated with glucose oxidase. No current response could be detected in this case. Therefore, non-specific oxidation of glucose at the electrode surface did not occur.

(3) Biosensors Based on Thin Latex Layers

Enzyme electrodes based on latex layers of 1 μm thickness showed a relatively low activity (approximately 10±2 nA/mM glucose). However, the dynamic range was very good. The current response to glucose was virtually linear in the measured range of 0–20 mM (FIG. 9). The response time increased with the amount of charge passed during pyrrole polymarization. The time to reach a steady-state current was less than a minute for the lowest polypyrrole content (100 $mC/cm^2$). When more 400 $mC/cm^2$ of charge was passed during the polymerization, no biosensor activity was found for the resulting enzyme treated electrodes. This probably will be due to the fact that no interspherical polypyrrole surface is available anymore for enzyme absorption. In the range of 100–300 $mC/cm^2$, the biosensor activity was virtually equal. For clarity, only one of these curves (corresponding to the sensor with 300 mC charge passed) is shown in FIG. 9. Also shown in FIG. 9 is the activity profile for a biosensor with an amount of polypyrrole corresponding to 400 $mC/cm^2$. The dynamic range of the sensor is much lower in this case. The use of 500 $mC/cm^2$ or more yielded enzymatically inactive membranes. The enzyme activity assay (Table B) showed similar activity tendencies. No significant difference in activity was found for latex membranes composed of 112 and 220 nm spheres respectively in case of these thin layers. The accessability of the membrane to glucose oxidase seems to be a critical factor. One the pores become too small, the enzyme cannot penetrate the membrane structure anymore and immobilization does not occur.

Smaller amounts of charge than 100 $mC/cm^2$ were not investigated because the polymerization time then became too short for reproducible results. Although low current densities were used (20 $mA/cm^2$), the polymerization time for charges under 100 $mC/cm^2$ is too short (less then 5 s) for the galvanostat. The ratio of the time to reach a constant current and the actual time the polymerization is under galvanostatic control becomes too large. During stabilization the polymerization reaction is not under galvanostatic control. This results in poorly defined polymerization conditions when the polymerization time is very short.

The reproducibility of the polypyrrole latex membrane biosensor construction was tested by repeating the experimental conditions for sensor construction. In FIG. 10 the result is shown for two membranes, containing an amount of polypyrrole corresponding to 150 $mC/cm^2$. The calibration lines are very similar, especially at low glucose concentrations.

(4) Biosensors Based on Thick Latex Layers

Thick layers (5 μm) consisting of 112 nm latex particles showed biosensor activity when treated with amounts of polypyrrole corresponding to 200–500 $mC/cm^2$. The same values apply for layers consisting of 220 nm particles. This is in concurrence with the data in Table B, where the enzymatic activity of these layers is listed. However, significant differences in the absolute values of biosensor activity were measured when the two types of latex layers (viz. with 112 and 220 nm spheres resp.) were treated with various amounts of polypyrrole. In FIG. 11 the calibration curves are shown for enzyme electrodes composed of 112 nm diameter latex particles and amounts of polypyrrole corresponding to 200 and 400 $mC/cm^2$ respectively. Lower amounts of polypyrrole were not tested (see also Table B). A polymerization time corresponding to 500 $mC/cm^2$ yielded no biosensor activity. The rotating disk assay showed some activity in this case (Table B), but probably the amount of enzyme present was no in direct contact with the conducting polymer. Consequently, no biosensor activity was measured.

Latex membranes with 220 nm particles showed somewhat different behavior. Pyrrole deposition corresponding to 500 $mC/cm^2$ still yielded biosensor activity, while higher polypyrrole loading yielded inactive membranes (FIG. 11b). The optimum in FIG. 11b is for membranes with an amount of polypyrrole corresponding to a change of 400 $mC/cm^2$. Lower amounts of polypyrrole yielded less active and poorly performing membranes.

The same discussion as for thin latex layers also applies for these 5 μm latex layers concerning the accessability for GOd. When too much polypyrrole is deposited the porosity of the latex membrane is lost and the enzyme cannot penetrate the membrane anymore. There is an optimum in the amount of incorporated polypyrrole, as shown in FIG. 11b. Lower polypyrrole loading yields less polymer surface for enzyme absorption, leading to less active sensors.

The optimum activity of sensors based on 5 μm membranes is approximately 60 +/− 10 nM glucose (calculated from the linear area). This can be compared to the activity of the 1 μm membranes (10 nA/mM glucose). The enzyme loading of the thick membranes will be higher due to the availability of more conducting polymer surface, leading to an increased activity.

(5) Characterization of Optimized Latex-Polypyrrole Biosensors

The biosensors which displayed the highest activity (vide supra) were characterized further. The dynamic range of these biosensors was tested by measuring a large range of glucose concentrations and the lifetime under quasi-continuous operation was evaluated.

Steady state current measurements were made in the same way as described above. Glucose concentrations up to 80 mM were measured. FIG. 12a shows the response curve for a 1 μm latex layer with 220 nm particle size, covered with an amount of polypyrrole corresponding to 150 mC/cm$^2$. In this case the current response to glucose was virtually linear up to 20 mM. The various amounts of polypyrrole on 112 and 220 nm particles tested gave similar calibration lines as in FIG. 12a. This reproducable behavior is lost upon going to 5 μm thick latex membranes. For the optimal latex-polypyrrole combinations a large difference in dynamic response is obtained for the different dimensions of the latex particles (FIG. 12b). The dynamic range of sensors based on 220 nm particles is 60 mM, with a linear current response to glucose up to 10 mM (FIG. 12b, solid line). From FIG. 12b (dashed line) it can be seen that the calibration curve for the sensor with 112 nm latex beads reveals a dynamic range of about half this value. The linearity on glucose concentration is less than 5 mM.

The response time of the biosensors depended on the amount of polypyrrole present, the thickness of the latex layer, and the particle size of the latex beads. The various response times were evaluated by measuring 5 mM glucose and are summarized in Table C. The response time is defined as the time needed to reach 95% of the steady state current. It should be noted that this time is slightly dependent on glucose concentration. However, the difference in response time for the measurement of, e.g., 2 mM and 20 mM glucose was less than approximately 5 s.

Selectivity and Lifetime

The sensitivity of the sensor to fructose, citrate, lactate, urea, uric acid and pyruvate was tested separately. No significant response was observed to any of these components when they were present at concentrations of 5 mM. Ascorbate (vitamin C), a common interferent in amperometric biosensors, interfered strongly when present at 5 mM concentration. However, in real sample the ascorbate concentration is usually much lower, e.g. in milk; 0.1 mM. The current response of freshly prepared biosensors was tested for prolonged periods of time. The sensors were taken up in a flow system which was at room temperature. The carrier stream contained 2 mM glucose. Therefore, this concentration of glucose was continuously measured during the lifetime experiment. To determine the biosensor activity a glucose concentration of 5 mM was introduced in the carrier stream and the increase in current was measured. In this way we were able to account for any deviations due to baseline drift and still the sensor lifetime was evaluated under continuous operation. In FIG. 13 the sensitivity of a latex-polypyrrole biosensor (220 nm, thick layer, 400 mC/cm$^2$) to 5 mM glucose is plotted as a function of time. The current response is not stable during the first days of measurement. Probably, in the beginning an amount of enzyme which is less firmly bound is slowly washed out. After 3 days, the sensor response remained the same for 10 days. This stability is sufficient for disposable applications.

Electrochemical Analysis of the Latex Biosensor

Measurements of biosensor activity were performed under argon at low potentials (0.10–0.35 V) in a continuous flow system. No additional mediators were present and any flavine cofactor, dissociated from the enzyme, would be washed out immediately. Therefore, the accidental mediation of electron transfer by free flavine molecules was not possible. The only low molecular weight mediator that could still be present in the system is oxygen. However, we found no significant difference in activity when measurements under ambient atmosphere were compared with measurements under argon. FIG. 14 shows a typical plot of the response (0.35 V vs. Ag/AgCl) under an argon atmosphere and the use of argon flushed solutions (solid line) and under ambient atmosphere with air saturated solutions (dashed line). The difference is less than 6% and is within the range of experimental error.

Oxygen competition would lead to hydrogen peroxide formation. At sufficiently low anodic potentials this would cause a strongly negative response, because $H_2O_2$ is reduced. This causes a large catalytic current to flow as is shown in FIG. 15, in which the response of a sensor membrane to 10 mM glucose is compared with the response of the same membrane to 0.0025% $H_2O_2$ at a potential of 0.10 V vs. Ag/AgCl. Due to the addition of $H_2O_2$ a very large negative current flows (FIG. 15). However, the addition of glucose still leads to a positive response. The formation of even the smallest mount of hydrogen peroxide during enzymatic glucose oxidation would have eliminated or probably inverted the current response to glucose. Therefore, we can conclude that no significant oxygen mediation takes place and that the measured current is due to direct communication between glucose oxidase and polypyrrole.

Considering the fact that the conducting polymer mediated the electron transport from the enzyme directly (i.e. no additional mediators were present), the working potential (maximum 0.35 V versus Ag/AgCl reference) of the latex-polypyrrole membrane electrodes was very low. Polypyrrole is electroactive in its oxidized state and the charge carried by the conducting polymer can be cycled repetitively. The confined space in the interspherical pores of the latex apparently brings the active centers of the enzyme molecules in close contact with the conducting polymer. The adsorption process should play an important role in this by allowing the enzyme to penetrate the surface of polypyrrole.

Applicant has found that drying after enzyme treatment of the membrane was essential for both the immobilization of enzymes and the direct electron transfer. Water is likely to be a competing species with regard to adsorption on the polymer surface. When water is removed by evaporation, enzyme adsorption is favoured and the active centers of the enzyme can approach the conducting polymer sufficiently to make direct communication possible. Electrostatic interactions could also play an important role in the immobilization process. Polypyrrole in its conducting state is a polycation. Glucose oxidase in neutral solution has in its turn at least 10 negative charges on its surface (pI is 4.1). Therefore, electrostatic interactions may be very strong. Because of these features the electroactive sites on the conducting polymer could strongly interact with the enzyme thereby making direct electron transfer possible.

Conclusions

Amperometric glucose biosensors can be constructed from polypyrrole modified latex layers which are cast on a platinum electrode. Adsorption of glucose oxidase on the interspherical polypyrrole surface leads to immobilization of the redox protein without loss of enzymatic activity. the response to glucose of this biosensor probably is the result of direct electron transfer between glucose oxidase and polypyrrole. The confined space in the pores between the latex spheres, together with the surface morphology of polypyrrole make this possible. Electrostatic interactions contribute to this property. Measurements under argon and oxygen atmosphere show no significant difference in current response. The response to hydrogen peroxide at relatively low anodic potential (i.e. 0.10 V vs. Ag/AgCl) is negative, while the glucose response is positive at this potential. This reveals that oxygen mediation does not take place. The absence of $H_2O_2$ production and the stabilisation of the enzyme by the special polypyrrole environment results in a biosensor with a considerable lifetime under continuous use.

The principle of immobilizing redox enzymes by adsorption on a conducting polymer surface inside the pores of latex layers can be applied to many combinations of redox enzymes and conducting polymers. The principle of sensor construction can be utilized to develp disposable sensors. The stability of the senosor is sufficient for this purpose.

We claim:

1. An electrode comprising a membrane having open pores running through said membrane, the walls of the pores having an electrically conducting polymer coating applied thereto, which polymer coating is in direct electronic contact with a redox enzyme bound thereto; said redox enzyme converting to one of an oxidized form and a reduced form upon reacting with a selected substrate, and said electrically conducting polymer participating in direct electron transfer with said redox enzyme to regenerate the other of said oxidized form and reduced form; and wherein said pores of said membrane remain open following application thereto of said polymer coating.

2. The electrode according to claim 1, wherein one side of the membrane has been provided with a conducting layer, which layer is in contact with the polymer coating.

3. The electrode according to claim 2, wherein the conducting layer is made of a noble metal or carbon.

4. The electrode according to claim 3, wherein the conducting layer is made of platinum.

5. The electrode according to claim 3, wherein the conducting layer has a thickness of 100–500 nm.

6. The electrode according to claim 1, wherein the membrane consists of a porous inert polycarbonate or polyester material.

7. The electrode according to claim 6, wherein the membrane is provided with pores having a diameter of 100–1000 nm and has a porosity of $1 \times 10^5 - 3 \times 10^8$ pores/$cm^2$.

8. The electrode according to claim 1, wherein the membrane is formed from latex particles.

9. The electrode according to claim 8, wherein the latex particles have a diameter in the range of 50–1000 nm.

10. The electrode according to claim 9, wherein the latex particles have a diameter in the range of 50–300 nm.

11. The electrode according to claim 8, wherein the latex is a polystyrene latex or a polymethyl methacrylate latex.

12. The electrode according to any one of the claims 8–10, wherein the latex is a silica latex.

13. The electrode according to claim 1, wherein the electrically conducting polymer is polypyrrole.

14. The electrode according to claim 13, wherein the polypyrrole coating has a thickness of 50–200 nm.

15. The electrode according to claim 1, wherein the redox enzyme is an oxidase.

16. The electrode according to claim 15, wherein the redox enzyme is a dehydrogenase.

* * * * *